(12) United States Patent
Tsubota et al.

(10) Patent No.: US 9,204,855 B2
(45) Date of Patent: Dec. 8, 2015

(54) PORTABLE RADIATION IMAGING APPARATUS AND PORTABLE RADIATION IMAGING SYSTEM

(71) Applicant: FUJIFILM Corporation, Tokyo (JP)

(72) Inventors: Keiji Tsubota, Ashigarakami-gun (JP); Naoyuki Nishino, Ashigarakami-gun (JP); Yasunori Ohta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/471,012

(22) Filed: Aug. 28, 2014

(65) Prior Publication Data

US 2015/0078529 A1 Mar. 19, 2015

(30) Foreign Application Priority Data

Sep. 17, 2013 (JP) .................................. 2013-192467
Feb. 19, 2014 (JP) .................................. 2014-029990

(51) Int. Cl.
*A61B 6/00* (2006.01)
*H04W 76/04* (2009.01)
*H04W 76/02* (2009.01)

(52) U.S. Cl.
CPC ............... *A61B 6/563* (2013.01); *A61B 6/4405* (2013.01); *H04W 76/02* (2013.01); *H04W 76/04* (2013.01)

(58) Field of Classification Search
CPC ...... A61B 6/563; A61B 6/548; A61B 6/4405; A61B 6/4283; H04W 76/02; H04W 76/04; H04W 88/08; G01T 1/17

USPC .......................................................... 250/394
See application file for complete search history.

(56) References Cited

U.S. PATENT DOCUMENTS

| 7,508,915 | B2 * | 3/2009 | Amitani et al. ............... 378/98.8 |
| 2006/0242552 | A1 * | 10/2006 | Tanaka ........................ 715/500.1 |
| 2010/0169423 | A1 * | 7/2010 | Eguchi .......................... 709/204 |
| 2010/0244574 | A1 * | 9/2010 | Nishino et al. ................... 307/80 |
| 2012/0051521 | A1 * | 3/2012 | Nishino ........................ 378/98.5 |
| 2013/0168568 | A1 * | 7/2013 | Watanabe ..................... 250/394 |

FOREIGN PATENT DOCUMENTS

| JP | 2002-125960 A | 5/2002 |
| JP | 2006-95212 A | 4/2006 |
| WO | WO 2009/031411 A1 | 3/2009 |

* cited by examiner

*Primary Examiner* — Marcus Taningco
(74) *Attorney, Agent, or Firm* — Birch, Stewart, Kolasch & Birch, LLP

(57) ABSTRACT

A portable X-ray imaging apparatus has an electronic cassette and a console capable of receiving an imaging order. The console has a wireless communication section, a trigger signal obtaining section, a connection determining section, a switching section, and a delivery requesting section. The wireless communication section receives radio waves and connects itself to an access point (AP). The trigger signal obtaining section obtains a trigger signal while the mobile radiography unit stands still. At the time of obtaining the trigger signal, the connection determining section determines one of the APs as an appropriate AP based on field intensity. The switching section switches the connection to the appropriate AP. Then, the delivery requesting section transmits a delivery request for the imaging order.

17 Claims, 18 Drawing Sheets

PORTABLE RADIATION IMAGING APPARATUS AND PORTABLE RADIATION IMAGING SYSTEM

CROSS-REFERENCE TO RELATED APPLICATIONS

The present application claims priority under 35 U.S.C. §119 to Japanese Patent Application No. 2013-192467, filed Sep. 17, 2013 and Japanese Patent Application No. 2014-029990, filed Feb. 19, 2014. Each of the above applications is hereby expressly incorporated by reference, in its entirety, into the present application.

BACKGROUND OF THE INVENTION

1. Field of the Invention

The present invention relates to a portable radiation imaging apparatus and a portable radiation imaging system.

2. Description Related to the Prior Art

In a medical field, radiation imaging systems which utilize radiation (for example, X-rays) are known. The X-ray imaging system comprises an X-ray generating apparatus and an X-ray imaging apparatus. The X-ray generating apparatus generates X-rays. The X-ray imaging apparatus detects the X-rays that passed through the subject (patient) and thereby captures an X-ray image of the subject. The X-ray generating apparatus has an X-ray source, a source control device, and an exposure switch. The X-ray source emits the X-rays to the subject. The source control device controls the X-ray source. The exposure switch inputs a command for operating the X-ray source to the source control device. The X-ray imaging apparatus has an X-ray image detection device and a console. The console issues operation commands to the X-ray image detection device, displays an X-ray image, and the like.

The X-ray image detection device has a sensor panel, which is also referred to as a flat panel detector (FPD). The sensor panel converts the X-rays that passed through the subject into an electric signal and thereby detects an X-ray image. The X-ray image detection device immediately transmits the detected X-ray image to the console to display the X-ray image thereon. In comparison with a conventional X-ray image recording device such as an X-ray film or an IP (imaging plate) cassette, the X-ray image detection device offers a user an advantage of viewing the image immediately after the image capture.

There are stationary X-ray image detection devices and portable X-ray image detection devices. The stationary X-ray image detection device is disposed in an imaging room. The portable X-ray image detection device (referred to as an electronic cassette) comprises a sensor panel and a portable housing which accommodates the sensor panel. The electronic cassette is used in combination with a portable console to constitute a portable X-ray imaging apparatus. In the imaging room, the electronic cassette may be attached to a stationary imaging support on which a subject (patient) in a standing position or lying position is imaged. The electronic cassette is also used for portable or bedside imaging, which is X-ray imaging performed in a hospital room of a patient who is incapable of coming to the imaging room, during a ward round.

There are also portable types of X-ray generating apparatuses. One type of the portable X-ray generating apparatuses is a movable X-ray generating apparatus with a movable cart on which the X-ray generating apparatus is mounted. The movable X-ray generating apparatus may be referred to as the mobile radiography unit. The portable X-ray imaging apparatus is mounted on the mobile radiography unit and moved to make the rounds at the hospital rooms, to perform portable imaging (for example, see Japanese Patent Laid-Open Publication Nos. 2002-125960 and 2006-095212).

The X-ray imaging is performed based on an imaging order, that is, information of a request for radiation imaging issued from a medical department such as internal medicine or surgery. The imaging order contains patient information (e.g. the name and the patient ID of a patient), the body part to be imaged, the purpose of imaging, and the like. A radiologic technologist performs the radiation imaging based on the imaging order. The imaging order is managed by a RIS (Radiology Information System) server. The portable X-ray imaging apparatus accesses the RIS server through a terminal such as a console and thereby obtains the imaging order.

The portable X-ray imaging apparatus disclosed in the Japanese Patent Laid-Open Publication Nos. 2002-125960 and 2006-095212 has a wireless terminal with a wireless communication function. The portable X-ray imaging apparatus uses the wireless terminal to access the RIS server through a LAN (Local Area Network) and thereby obtains the imaging order. The LAN is provided with access points, which are wireless relay stations allowing the wireless terminal to connect to the LAN. The access points are provided at important locations in a ward in which the portable imaging is performed, allowing the wireless terminal to obtain the imaging order during the ward round through the hospital rooms.

The access point constantly transmits radio waves called a beacon signal to notify the wireless terminal of its presence. The wireless terminal receives the beacon signal and thereby identifies the presence of the access point, and connects itself to the identified access point. The wireless terminal maintains the connection to the access point, which transmits the beacon signal, as long as the wireless terminal receives the beacon signal. The wireless terminal is disconnected from the access point when the wireless terminal is out of a range (coverage) of the beacon signal. Naturally, in a case where there are two or more access points, the communication quality is stable when the connection to the access point with higher field intensity than the others is established. A technique to compare the field intensities of the access points and automatically switch the connection to the access point with high field intensity is known (for example, see U.S. Patent Application Publication No. 2010/0169423 corresponding to WO 2009/031411).

The U.S. Patent Application Publication No. 2010/0169423 discloses an electronic cassette having a wireless communication function. In a case where the electronic cassette is moved through imaging rooms, the electronic cassette compares the field intensities of the access points, and switches its connection automatically to the access point with high field intensity (paragraph 0072).

The technique for automatically switching the connection to the access point with high field intensity as disclosed in the U.S. Patent Publication Application No. 2010/0169423 is referred to as roaming. As described above, the ward round is made to perform the portable imaging with the use of the mobile radiography unit, on which the portable X-ray imaging apparatus is mounted. Well-functioning roaming is convenient for constantly ensuring the stable communication quality.

At the start of the portable imaging, first, the console is operated to access the RIS server and obtain imaging order(s) in a cart parking area, in which the mobile radiography unit is parked. After the imaging order is obtained, the portable X-ray imaging apparatus is mounted on the mobile radiography unit. The radiologic technologist with the mobile radiography unit is headed for the ward and makes the ward round through the hospital rooms. An additional imaging order may occur during the ward round. By accessing the RIS server, the additional imaging order is obtained in the ward. Failure in receiving the additional imaging order requires the radiologic technologist to return to the hospital room of the patient who has finished radiation imaging, and perform re-imaging of the patient.

To avoid such trouble, inventors have examined the provision of a function to transmit a delivery request for the imaging order by accessing the RIS server through an access point and a roaming function, to the console having the wireless communication function. Transmitting the delivery request for the imaging order at regular time intervals prevents the failure in receiving the additional imaging order even if the additional imaging order occurs during the ward round. The roaming function automatically switches the connection to the access point with high field intensity. Thus, the communication quality becomes stable, preventing the reception error of the imaging order.

However, experiments revealed that the sole provision of the roaming function as disclosed in the U.S. Patent Application Publication No. 2010/0169423 cannot prevent roaming problems such as failure in switching the connection to an appropriate access point. For example, in a case where the mobile radiography unit is moved from a first floor to a second floor of a ward, the console is connected to an access point on the first floor with high field intensity while the mobile radiography unit is on the first floor. When the radiography unit with the console is moved to the second floor, the field intensity of an access point on the second floor is higher than that of the access point on the first floor. If the roaming works properly, the console switches its connection to the access point with high field intensity on the second floor. However, in actual cases, the console often maintains its connection to the access point on the first floor and does not switch its connection to the access point on the second floor in a case where the radio waves from the access point on the first floor reach the second floor.

The inventors considered one of the reasons for the roaming problems as follows. The roaming function as disclosed in the U.S. Patent Application Publication No. 2010/0169423 detects the field intensities of the access points and compares the detected field intensities with each other while the mobile radiography unit is on the move. In this case, the field intensities vary with the move of the mobile radiography unit, so that the detection may not be accurate. Once the detection of a change in the field intensity is failed, a cue for switching the connection to the appropriate access point is lost. This causes the roaming problem, namely, the connection to the currently-connected access point is maintained despite the presence of another appropriate access point. There is another factor for causing the roaming problems. Recently, mobile wireless terminals have been rapidly prevailing in medical facilities. Although accurate measurement of the field intensity is indispensable for appropriate roaming, it is becoming more difficult due to interference from the increasing wireless terminals.

The failure (reception error) in receiving a new or additional imaging order for the portable imaging during the ward round increases burdens on the radiologic technologist, so that they strongly demand countermeasures to avoid the reception error. According to a survey conducted by the inventors, there are about 20 imaging orders plus up to 30 or more emergency imaging orders for the portable imaging per day. The portable imaging is normally performed by one radiologic technologist. The radiologic technologist may perform the portable imaging of up to 50 or more images in one day. A single imaging procedure may take approximately 5 minutes. However, the patient who is the subject of the portable imaging often has difficulty in moving his/her body, so that positioning, such as raising the upper part of the body of the patient and placing the electronic cassette at an appropriate position, takes a long time. The failure in receiving the additional imaging order increases the burdens on the radiologic technologist because he/she needs to return to the hospital room which he/she has left and do the positioning or the like all over again.

The Japanese Patent Laid-Open Publication Nos. 2002-125960 and 2006-095212 and the U.S. Patent Publication Application No. 2010/0169423 do not point out explicitly or suggest the above-described problems and their solutions. The U.S. Patent Application Publication No. 2010/0169423 discloses that the electronic cassette performs roaming based on the field intensity. However, it only discloses the general art of roaming and does not clearly disclose configuration and procedure of the roaming.

SUMMARY OF THE INVENTION

An object of the present invention is to provide a portable radiation imaging apparatus and a portable radiation imaging system, capable of preventing failure in receiving an additional imaging order in a case where the imaging order is received through wireless communication.

In order to achieve the above and other objects, the portable radiation apparatus according to the present invention comprises a wireless communication section, a trigger signal obtaining section, a connection determining section, a switching section, and a delivery requesting section. The wireless communication section receives radio waves from an access point and establishes connection to the access point. The trigger signal obtaining section obtains a trigger signal at least one time from a trigger signal source that transmits the trigger signal, in a state where the portable radiation imaging apparatus stands still. The connection determining section obtains the trigger signal and then determines one of the access points as an appropriate access point based on field intensity in a case where the wireless communication section receives the radio waves from the access points. The switching section commands the wireless communication section to switch the connection to the appropriate access point in a case where the wireless communication section is not connected to the appropriate access point, and allows the wireless communication section to maintain the connection in a case where the wireless connection section is connected to the appropriate access point. The delivery requesting section transmits a delivery request for an imaging order to an imaging order managing device through the wireless communication section in a state where the wireless communication section is connected to the appropriate access point. The portable radiation imaging apparatus is used in combination with a portable radiation generating apparatus. The portable radiation imaging apparatus accesses the imaging order managing device, which manages the image order, through the access point, being a wireless relay station, and obtains the imaging order, being information of a request for radiation imaging.

It is preferable that the trigger signal source is at least one of a first transmitting section provided in the portable radiation imaging apparatus and a second transmitting section provided to the portable radiation generating apparatus.

It is preferable that the portable radiation imaging apparatus further comprises, for example, an electronic cassette for detecting a radiation image and a console having a function to display the imaging order and the radiation image.

It is preferable that the console has, for example, the wireless communication section, the trigger signal obtaining section, the connection determining section, the switching section, the delivery requesting section, and a function to receive the imaging order.

It is preferable that the first transmitting section transmits the trigger signal when the electronic cassette is ready for imaging. The first transmitting section may transmit the trigger signal when the console is operated.

It is preferable that the trigger signal obtaining section obtains the trigger signal, which is transmitted from the second transmitting section, through communication with the portable radiation generating apparatus.

It is preferable that the portable radiation generating apparatus is a movable radiation generating apparatus comprising, for example, a radiation source for applying radiation and a cart on which the radiation source is mounted. The movable radiation generating apparatus has, for example, a locking mechanism for limiting displacement of the radiation source while the cart is moved. The second transmitting section transmits the trigger signal when the locking mechanism is unlocked.

It is preferable that the movable radiation generating apparatus has, for example, a stop sensor for detecting that the cart is stopped. The second transmitting section transmits the trigger signal when the stop sensor detects that the cart is stopped.

It is preferable that the movable radiation generating apparatus has, for example, an accommodation section for accommodating the electronic cassette and a removal detection sensor for detecting that the electronic cassette is taken out of the accommodation section. The second transmitting section transmits the trigger signal when the removal detection sensor detects that the electronic cassette is taken out.

It is preferable that the first transmitting section or the second transmitting section transmits the trigger signal when positioning of the electronic cassette relative to a subject is completed, for example. The first transmitting section or the second transmitting section transmits the trigger signal at least one time after the portable radiation imaging apparatus stops moving and before single imaging ends.

It is preferable that the first transmitting section or the second transmitting section transmits the trigger signal in response to at least one of steps, before an end of single imaging, included in a work flow of portable imaging. It is preferable that the steps are those performed before positioning of the electronic cassette.

It is preferable that the delivery requesting section transmits the delivery request at regular time intervals regardless of presence or absence of the trigger signal.

The portable radiation imaging system according to the present invention comprises a portable radiation generating apparatus and a portable radiation imaging apparatus used in combination with the portable radiation generating apparatus. The portable radiation imaging apparatus accesses an imaging order managing device, which manages an image order, through an access point, being a wireless relay station, and obtains the imaging order, being information of a request for radiation imaging. The portable radiation imaging system further comprises a wireless communication section, a trigger signal obtaining section, a connection determining section, a switching section, and a delivery requesting section. The wireless communication section receives radio waves from the access point and establishes connection to the access point. The trigger signal obtaining section obtains a trigger signal at least one time from a trigger signal source that transmits the trigger signal, in a state where the portable radiation imaging apparatus stands still. The connection determining section obtains the trigger signal and then determines one of the access points as an appropriate access point based on field intensity in a case where the wireless communication section receives the radio waves from the access points. The switching section commands the wireless communication section to switch the connection to the appropriate access point in a case where the wireless communication section is not connected to the appropriate access point, and allows the wireless communication section to maintain the connection in a case where the wireless connection section is connected to the appropriate access point. The delivery requesting section transmits a delivery request for the imaging order to the imaging order managing device through the wireless communication section in a state where the wireless communication section is connected to the appropriate access point.

According to the present invention, the trigger signal is obtained while the portable radiation imaging apparatus stands still. At this time, one of the access points is determined as the appropriate access point based on the field intensity. The field intensity is measured accurately, ensuring the stable communication quality. Thus, the portable radiation imaging apparatus and the portable radiation imaging system capable of preventing failure in receiving the new or additional imaging order is provided.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
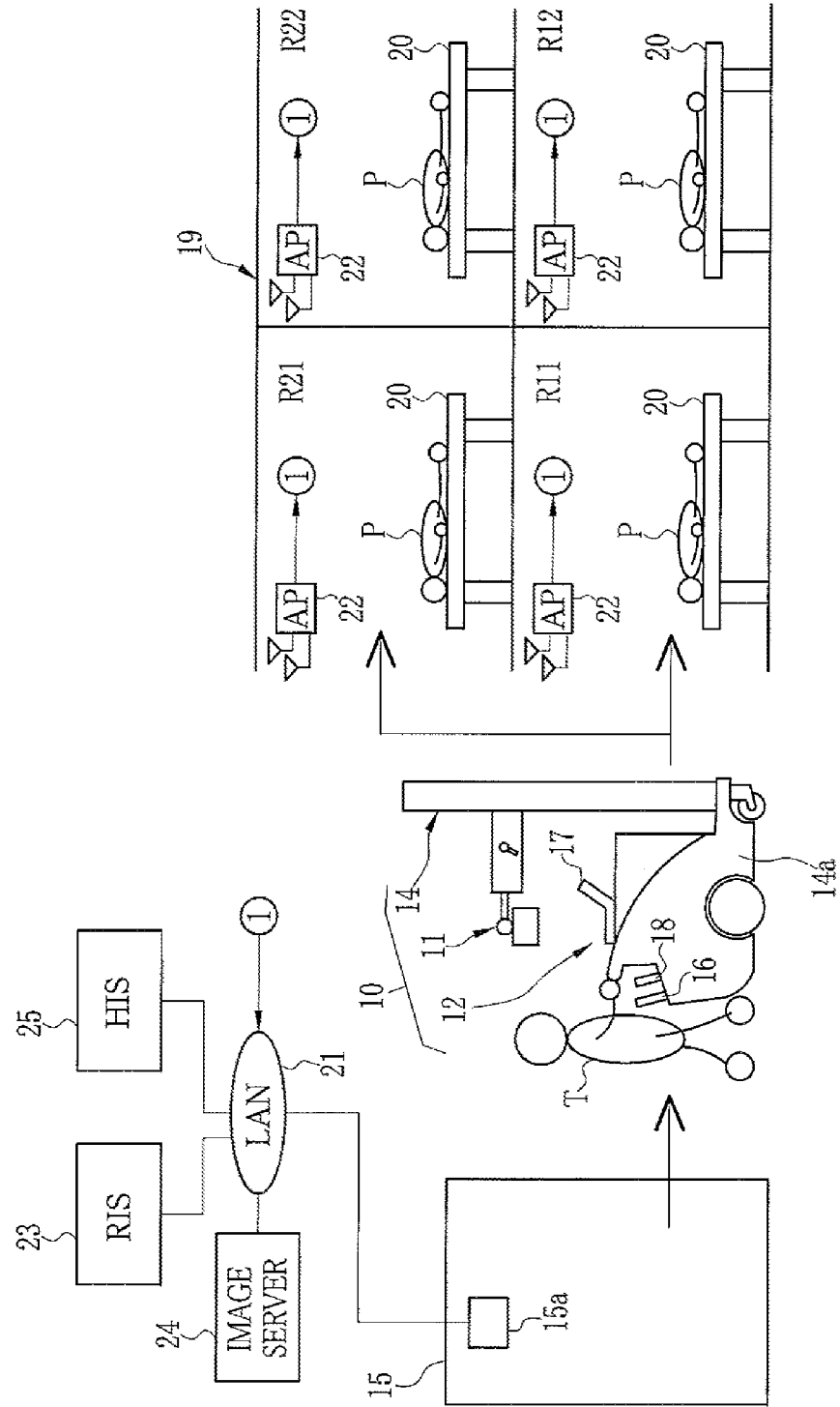
FIG. 1 is a schematic view illustrating a an X-ray imaging system and a ward in which portable or bedside imaging is performed.

In FIG. 1, a portable X-ray imaging system (hereinafter simply referred to as the X-ray imaging system) 10 is composed of a portable X-ray generating apparatus (hereinafter, simply referred to as the X-ray generating apparatus) 11 and a portable X-ray imaging apparatus (hereinafter, simply referred to as the X-ray imaging apparatus) 12. The X-ray generating apparatus 11 is a movable (mobile) X-ray generating apparatus mounted on a movable cart 14a that moves with wheels. The X-ray generating apparatus 11 together with the cart 14a is referred to as a mobile radiography unit 14. The X-ray imaging apparatus 12 has an electronic cassette 16, a portable console 17, and a functional unit 18, and is mounted on the mobile radiography unit 14. The mobile radiography unit 14 is placed in a cart parking area 15 in medical facilities or a hospital when not in use. At the time of portable or bedside imaging, the portable X-ray imaging apparatus 12 is mounted on the mobile radiography unit 14, and then the mobile radiography unit 14 is moved out of the cart parking area 15. A radiologic technologist (hereinafter, simply referred to as an operator) T pushes the mobile radiography unit 14 to make a ward round through hospital rooms R11, R12, R21, and R22 in a ward 19, and images each patient P, being a subject, at each bed 20.

An access point (abbreviated as AP) 22 is provided in each of the hospital rooms R11, R12, R21, R22, and other important locations in the hospital. The AP 22 is a wireless relay station for connecting a wireless terminal to a LAN (Local Area Network) 21 that is a communication network within the hospital. The AP 22 comprises a wireless communication section for wirelessly communicating with the wireless terminal and a cable communication section for connection to the LAN 21 through a communication cable. The wireless communication section is compliant with a wireless LAN standard such as IEEE 802.11n. The cart parking area 15 is provided with a LAN outlet 15a for cable connection to the LAN 21.

A HIS (HIS: Hospital Information System) server 25, a RIS (RIS: Radiology Information System) server 23, and an image server 24 are connected to the LAN 21.

The HIS server 25 is a server for managing electronic charts. Mainly, medical staffs (e.g. doctors and nurses) of medical departments (e.g. the department of surgery and the department of internal medicine) access the HIS server 25 through medical department terminals. The medical department terminals include desktop and notebook computers and portable wireless terminals (e.g. tablet computers) carried by the doctors and the nurses. The medical department terminals are used to view electronic charts and to input treatment information.

The RIS server 23 is a server managed by the radiology department. The RIS server 23 is an imaging order managing device that manages imaging orders. The imaging order is information of a request for radiation imaging, which is transmitted from a medical department to the radiology department. The imaging order contains requester information that includes the name of a doctor who requested imaging and the name of the medical department to which the doctor belongs, patient information that includes the patient's name, age, and gender, a body part (e.g. head, chest, abdomen (stomach), hand, or finger) to be imaged, an imaging direction, and a message that includes the purpose of the imaging and instructions or precautions from the doctor who made the imaging order. The imaging direction may be front, lateral, oblique, PA (posteroanterior; X-ray application from back to front through the body), AP (anteroposterior; X-ray application from front to back through the body), or the like. The operator T checks the content of the imaging order on the console 17 and determines imaging conditions suitable for the imaging order. The imaging conditions are set to the electronic cassette 16 and the X-ray generating apparatus 11.

The imaging conditions include irradiation conditions, which are determined by a tube voltage (unit; kV), a tube current (unit: mA), and irradiation time (exposure time) (unit: s) of the X-rays. The tube voltage determines energy spectrum of the X-rays emitted from an X-ray source 26 (see FIG. 2). The tube current determines an exposure amount (dose) of the X-rays per unit time. An accumulated dose is determined by the product of the tube current and the irradiation time. In some cases, the tube current-time product (mAs value), which is the product of the tube current and the irradiation time, may be inputted as the irradiation condition, instead of each of the tube current and the irradiation time.

The image server 24 manages image data such as X-ray images captured with the X-ray imaging apparatus 12 in accordance with the imaging orders. The image server is accessible from the medical department terminal from which the imaging order is transmitted. The doctor of the medical department accesses the image server 24 through the medical department terminal and views the captured X-ray image.

The console 17 of the X-ray imaging apparatus 12 is accessible to the RIS server 23 and the image server 24 through the LAN 21. The console 17 accesses the RIS server 23 and obtains the imaging order, and transmits the captured X-ray image to the image server 24. In the cart parking area 15, the console 17 is accessible to the RIS server 23 and the image server 24 through the cable-connection to the LAN outlet 15a. In the ward 19, the console 17 is accessible to the RIS server 23 and the image server 24 through the wireless connection to one of the APs 22. Note that the console 17 is accessible to the RIS server 23 and the image server 24 through the wireless connection to the AP 22 in a case where the cart parking area 15 is provided with the AP 22, instead of the cable-connection to the LAN outlet 15a.

Figure 2:
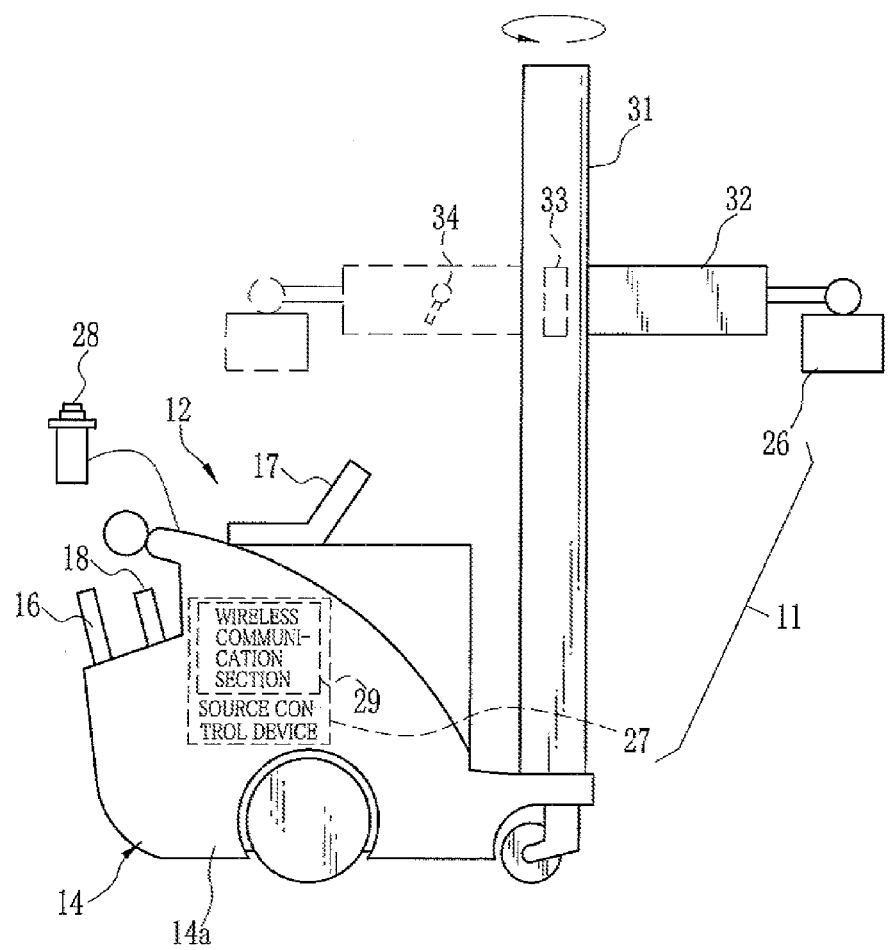
FIG. 2 is an explanatory view of a mobile radiography unit.

In FIG. 2, the X-ray generating apparatus 11 comprises the X-ray source 26, a source control device 27 for controlling the X-ray source 26, and an exposure switch 28. The X-ray source 26 has an X-ray tube (not shown) for emitting the X-rays and a collimator for limiting an X-ray field of the X-rays from the X-ray tube. The X-ray tube has a cathode and an anode (target). The cathode is composed of a filament that emits thermal electrons. The thermal electrons from the cathode impinge on the target and thereby the X-rays are emitted. The collimator is formed with, for example, a rectangular irradiation opening at its center. Four lead plates for blocking the X-rays are disposed on the respective sides of the rectangular opening. Shifting the lead plates changes the size of the irradiation opening and thereby limits the X-ray field.

A column 31 is mounted in a vertical direction on the mobile radiography unit 14. The column 31 is provided with an arm 32 that extends in a horizontal direction. The X-ray source 26 is attached to one end of the arm 32. The column 31 is rotatable around its longitudinal axis. The arm 32 and the X-ray source 26 are rotated by the rotation of the column 31. The arm 32 is moved up or down along the column 31. The X-ray source 26 is rotatably attached to the arm 32. The emission position and the direction of the X-ray source 26 are adjusted by the rotation of the column 31, the movements of the arm 32 in the up-down direction, and the rotation of the X-ray source 26. The column 31 is provided with a locking mechanism 33.

The locking mechanism 33 restricts movements (displacements) of the arm 32 and the X-ray source 26 so as to prevent inadvertent movements of the column 31, the arm 32, and the X-ray source 26 while the mobile radiography unit 14 is on the move. The locking mechanism 33 has a lock pin that moves between a locking position, at which the movement of the X-ray source 26 is restricted, and an unlocking position, at which the movement of the X-ray source 26 is allowed. A lock member 34 is operated to move the locking pin, and thereby locks or unlocks the locking mechanism 33. The locking mechanism 33 generates an unlocking signal when unlocked. The unlocking signal is transmitted to the source control device 27 through an internal cable.

The source control device 27 is composed of a high voltage generator, which supplies a high voltage to the X-ray source 26, and a controller for controlling a tube voltage, a tube current, and irradiation time (exposure time). The high voltage generator boosts an input voltage with a transformer and thereby generates a high tube voltage. The high voltage generator supplies drive power to the X-ray source 26 through a high voltage cable. The operator T manually sets the irradiation conditions such as the tube voltage, the tube current, and the irradiation time through an operation panel (not shown) of the source control device 27. The irradiation conditions may be transmitted from the console 17 to the source control device 27 and set to the source control device 27.

The exposure switch 28, which is connected to the source control device 27 through a signal cable, is operated by the operator T. The exposure switch 28 is a two-step switch. When pressed one step down, the exposure switch 28 generates a warm-up starting signal for allowing the X-ray source 26 to start warm-up. When pressed two steps down, the exposure switch 28 generates an exposure starting signal for allowing the X-ray source 26 to start the exposure. These signals are inputted to the source control device 27 through the signal cable.

The source control device 27 controls the operation of the X-ray source 26 based on the signal from the exposure switch 28. In a case where the source control device 27 receives the exposure starting signal from the exposure switch 28, the source control device 27 starts supplying power to the X-ray source 26, and activates a timer to start measuring the irradiation time. After a lapse of the irradiation time, which is set according to the irradiation conditions, the source control device 27 stops the X-ray irradiation. The irradiation time varies with the irradiation conditions. Maximum irradiation time for safety control is set to the source control device 27 in advance. The irradiation time, which is set based on the irradiation conditions, is less than or equal to the maximum irradiation time.

A wireless communication section 29 is provided in the source control device 27. The wireless communication section 29 is compliant with the wireless LAN standard, for example, IEEE 802.11n. The wireless communication section 29 transmits the unlocking signal, which is received from the locking mechanism 33, to the X-ray imaging apparatus 12.

Figure 3:
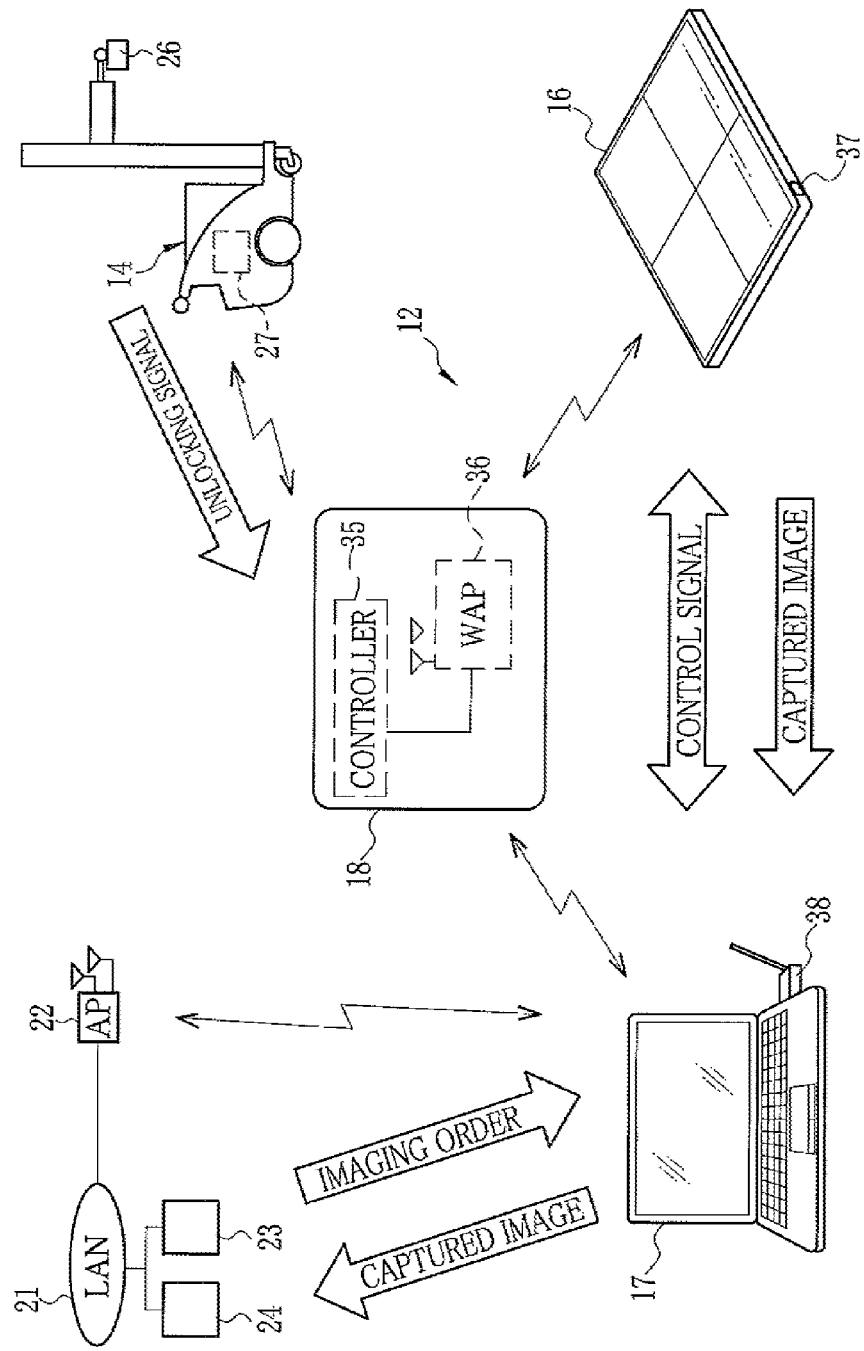
FIG. 3 is a schematic view of an X-ray imaging apparatus.

In FIG. 3, in the X-ray imaging apparatus 12, each of the electronic cassette 16, the console 17, and the functional unit 18 has a wireless communication section, so that they are capable of mutual wireless communication. The wireless communication section of the X-ray imaging apparatus 12 is compliant with the wireless LAN standard such as IEEE 802.11n, as in the case of the wireless communication section 29.

The functional unit 18 is provided with a controller 35 and a WAP (Wireless Access Point) 36. The controller 35 centrally controls each section of the functional unit 18. Each of the electronic cassette 16 and the console 17 is provided with wireless communication sections 37 and 38. The wireless communication between the console 17 and the electronic cassette 16 is performed by wirelessly connecting each of the wireless communication sections 37 and 38 to the WAP 36. As for data communication between the console 17 and the electronic cassette 16, the console 17 transmits imaging conditions and control signals including an operation signal such as an imaging preparation command, which are inputted by the operator T through the console 17, to the electronic cassette 16. The electronic cassette 16 transmits the response to the control signal from the console 17 and an X-ray image detected by the electronic cassette 16 to the console 17. The electronic cassette 16 is ready for imaging (hereinafter referred to as the "ready" state) upon receiving the imaging preparation command.

The console 17 is connected to the LAN 21 through the AP 22 or the WAP 36, and thereby accessible to the RIS server 23 and the image server 24. The WAP 36 relays the wireless communication between the console 17 and the source control device 27, which is incorporated in the mobile radiography unit 14. Thus, the irradiation conditions are transmitted wirelessly from the console 17 to the source control device 27. In this case, it is unnecessary to manually set the irradiation conditions to the source control device 27 through the operation panel of the mobile radiography unit 14. The X-ray imaging apparatus 12 may receive a signal which represents that the exposure switch 28 has been operated, from the source control device 27 through the WAP 36. Furthermore, the console 17 receives the unlocking signal from the source control device 27 through the WAP 36.

The electronic cassette 16 is composed of a sensor panel 41 (see FIG. 4) and a portable type housing for accommodating the sensor panel 41. The electronic cassette 16 is a portable X-ray image detection device that receives the X-rays emitted from the X-ray source 26 and passed through the patient P, being the subject, and thereby detects an X-ray image of the patient P. The housing has a flat panel-like shape. The size of the flat surface of the X-ray image detection device is substantially the same as those of the film cassette and IP cassette, for example.

Figure 4:
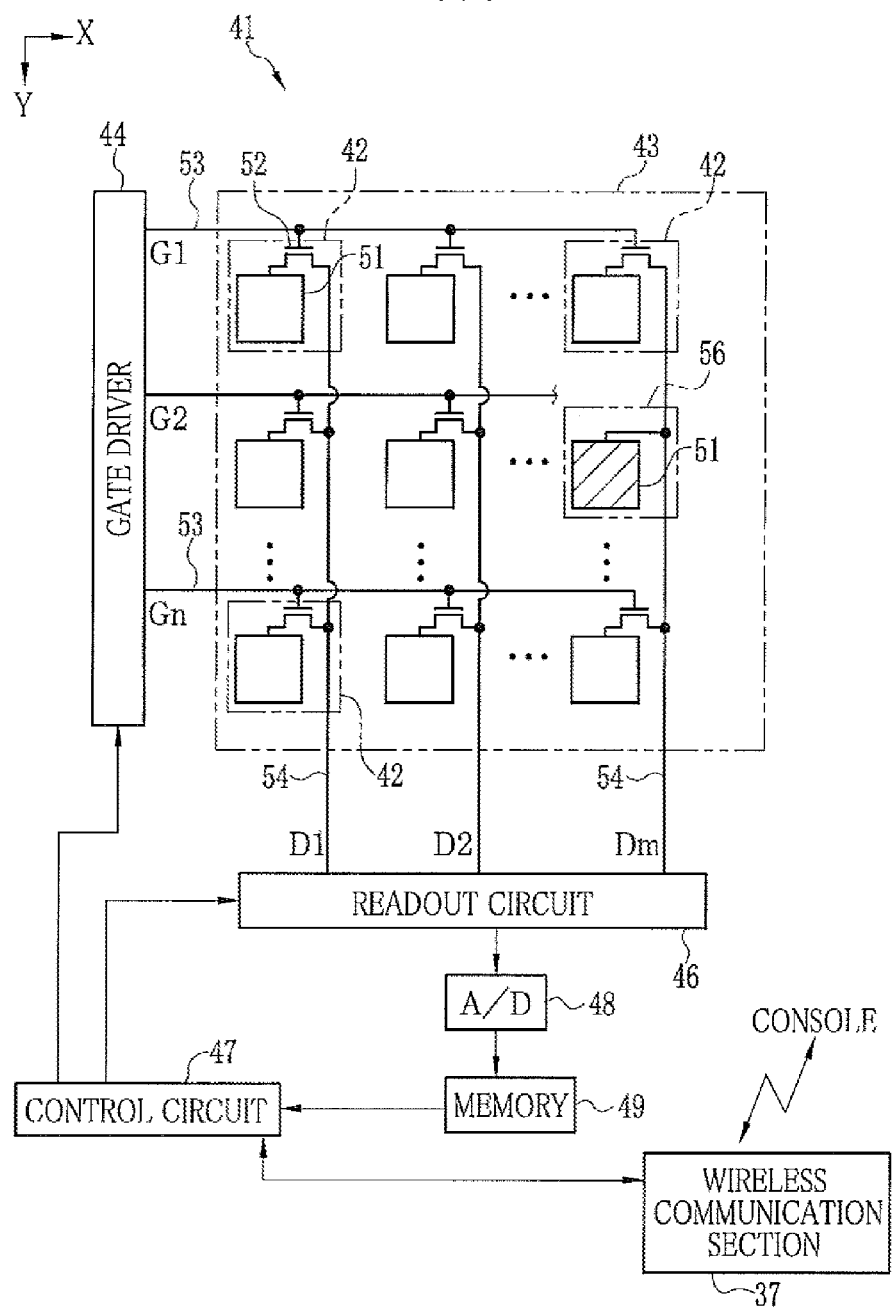
FIG. 4 is an explanatory view illustrating a sensor panel.

As shown in FIG. 4, the sensor panel 41 comprises a TFT active matrix circuit board formed with an image capture field 43, a gate driver 44, a readout circuit 46, a control circuit 47, an A/D converter 48, a memory 49, and the wireless communication section 37. A battery (not shown) for driving each section of the sensor panel 41 is accommodated in the housing.

In the image capture field 43, a plurality of pixels 42 are arranged in a matrix of n rows (X direction)×m columns (Y direction) at a predetermined pitch. Each pixel 42 stores a signal charge corresponding to the amount of the incident X-ray. Note that "n" is an integer of two or more, and "m" is an integer of two or more, for example, n, m≈2000. Note that the pixels 42 may not be arranged in a square. For example, the pixels 42 may be arranged in a honeycomb pattern. The sensor panel 41 has a scintillator (phosphor, not shown) that converts the X-rays into visible light. The sensor panel 41 is an indirect conversion type that photoelectrically converts the visible light, which is converted by the scintillator, with the use of the pixels 42. The scintillator is made from CsI:Tl (thallium-activated cesium iodide), GOS (Gd$_2$O$_2$S:Tb, terbium-activated gadolinium oxysulfide), or the like. The scintillator is disposed to face the entire image capture field 43 in which the pixels 42 are arranged. Instead of the indirect conversion type, note that the sensor panel 41 may be a direct conversion type that directly converts the X-rays into charges.

The pixel 42 comprises a photodiode 51, being a photoelectric conversion element, and a thin-film transistor (TFT) 52, being a switching element. The photodiode 51 generates a charge (electron-hole pair) upon incidence of the visible light. The photodiode is composed of a semiconductor layer (for example, PIN type) made from a-Si (amorphous silicon) or the like, and upper and lower electrodes above and below the semiconductor layer. The TFT 52 of the photodiode 51 is connected to the lower electrode. A bias voltage is applied to the upper electrode. With the application of the bias voltage, an electric field is generated in the semiconductor layer. The electrons and holes move toward the upper and lower electrodes with positive and negative polarities, respectively. Thus, the charges are stored in the photodiode 51, which also functions as a capacitor.

A gate electrode of the TFT 52 is connected to a scanning line 53. A source electrode of the TFT 52 is connected to a signal line 54. A drain electrode of the TFT 52 is connected to the photodiode 51. The scanning lines 53 and the signal lines 54 are arranged in a lattice pattern. The number of the scanning lines 53 corresponds to the number (n) of the rows of the pixels 42 in the image capture field 43. The number of the signal lines 54 corresponds to the number (m) of the columns of the pixel 42. The scanning lines 53 are connected to the gate driver 44. The signal lines 54 are connected to the readout circuit 46.

The gate driver 44 allows the sensor panel 41 to perform a storage operation, a readout operation, and a reset operation, through driving the TFTs 52 under control of the control circuit 47. In the storage operation, the signal charges corresponding to the dose of the incident X-rays are stored in the pixels 42. In the readout operation, the signal charges stored in the pixels 42 are read out. In the reset operation, unnecessary charges stored in the pixels 42 are eliminated. The gate driver 44 turns off all of the TFTs 52 of the pixels 42 during the X-ray irradiation. Thereby the gate driver 44 allows the pixels 42 to start the storage operation for storing the signal charges. After the X-ray irradiation ends, the gate pulses G1-Gn are inputted sequentially to the respective scanning lines 53, and thereby turn on the TFTs 52 on a row-by-row basis. Thus the readout operation for reading out the signal charges is performed. The signal charges read out from the pixels 42 are transmitted through the signal lines 54 to the readout circuit 46.

Dark charge occurs in the photodiode 51 regardless of the presence or absence of the incident X-rays. The dark charge is a noise to the image data. A reset operation is performed to eliminate the dark charges before the X-ray irradiation. The reset operation is to discharge the dark charges from the pixels 42 through the signal lines 54.

The readout circuit 46 reads out signal charges D1-Dm from the pixels 42. The control circuit 47 centrally controls each section. The A/D converter 48 converts the signal charge into digital data. The data converted by the A/D converter 48 is written into the memory 49.

The readout circuit 46 is composed of an integration amplifier and a multiplexer. The integration amplifier converts the signal charge, which is read out from the pixel 42, into a voltage signal. The multiplexer sequentially switches the columns of the pixels 42 in the image capture field 43 to sequentially output the voltage signal on a column-by-column basis.

In the readout operation, the A/D converter 48 converts the voltage signal, which is inputted to the readout circuit 46, into digital data. The digital data is written as digital image data into the memory 49. The image data read out from the memory 49 is transmitted to the console 17 through the wireless communication section 37.

In the reset operation, the TFTs 52 of the pixels 42 are sequentially turned on a row-by-row basis, in a manner similar to the readout operation. Thereby the dark charges are inputted from the pixels 42 to the readout circuit 46. In the reset operation, the dark charges are released by resetting the integration amplifier and not outputted to the A/D converter 48. The reset operation is started, for example, when the electronic cassette 16 is turned on, and repeated at regular time intervals. When the electronic cassette 16 is ready for imaging ("ready" state), the reset operation is temporarily stopped. Then, immediately before the start of the storage operation of the pixel 42, the reset operation for one screen is performed one time.

A detection sensor 56, which utilizes a part of the pixel 42, is provided in the image capture field 43. The detection sensor 56 detects the start of the X-ray irradiation. Similar to the pixel 42, the detection sensor 56 has the photodiode 51, but is not provided with the TFT 52. The photodiode 51 of the detection sensor 56 and the signal line 54 are short-circuited, so that the output (the amount of the charge generated in the photodiode 51) of the detection sensor 56 flows through the signal line 54 regardless of whether the TFT 52 is turned on or off.

The output of the detection sensor 56 is read out to the memory 49 through the readout circuit 46 and the A/D converter 48, as in the case of the pixel 42. The readout of the output of the detection sensor 56 is repeated in the order of p sec. The output of the detection sensor 56 per readout corresponds to the amount of the incident X-rays per unit time. After the start of the X-ray irradiation, the amount of the incident X-rays per unit time gradually increases, so that the output of the detection sensor 56 increases with the amount of the incident X-rays per unit time.

Every time the output of the detection sensor 56 is recorded in the memory 49, the control circuit 47 reads out the output and compares the output with a predetermined threshold value. The control circuit 47 determines that the X-ray irradiation is started when the output is greater than or equal to the threshold value, and thereby detects the start of the X-ray irradiation. Thus the sensor panel 41 itself detects the start of the X-ray irradiation without receiving a synchronization signal from the X-ray generating apparatus 11. The control circuit 47 is capable of reading out the output of the detection sensor 56 even during the storage operation of the sensor panel 41. Namely, the control circuit 47 is capable of detecting the end of the X-ray irradiation based on the output of the detection sensor 56.

After the electronic cassette 16 is turned on, the sensor panel 41 starts the reset operation of the pixels 42. Thereafter, upon receiving the imaging preparation command from the console 17, the sensor panel 41 stops the reset operation and becomes ready for imaging ("ready" state), and starts the start detecting operation, that is, reading the output of the detection sensor 56. Upon detecting the start of the X-ray irradiation, the sensor panel 41 performs the reset operation of one screen, and then turns off the TFTs 52 of the pixels 42 to start the storage operation. Furthermore, upon detecting the start of the X-ray irradiation, the sensor panel 41 transmits a start detection signal to the console 17 through the wireless communication section 37. The sensor panel 41 continues reading the output of the detection sensor 56 during the storage operation. The control circuit 47 determines that the X-ray irradiation is ended when the read output of is less than or equal to a predetermined threshold value, and thus detects the end of the X-ray irradiation. Upon detecting the end of the X-ray irradiation, the sensor panel 41 ends the storage operation and starts the readout operation of the X-ray image. In this example, the start and the end of the X-ray irradiation are determined using the threshold value for the start of the X-ray irradiation and the threshold value for the end of the X-ray irradiation, respectively. Note that the threshold values may be the same or different.

Figure 5:
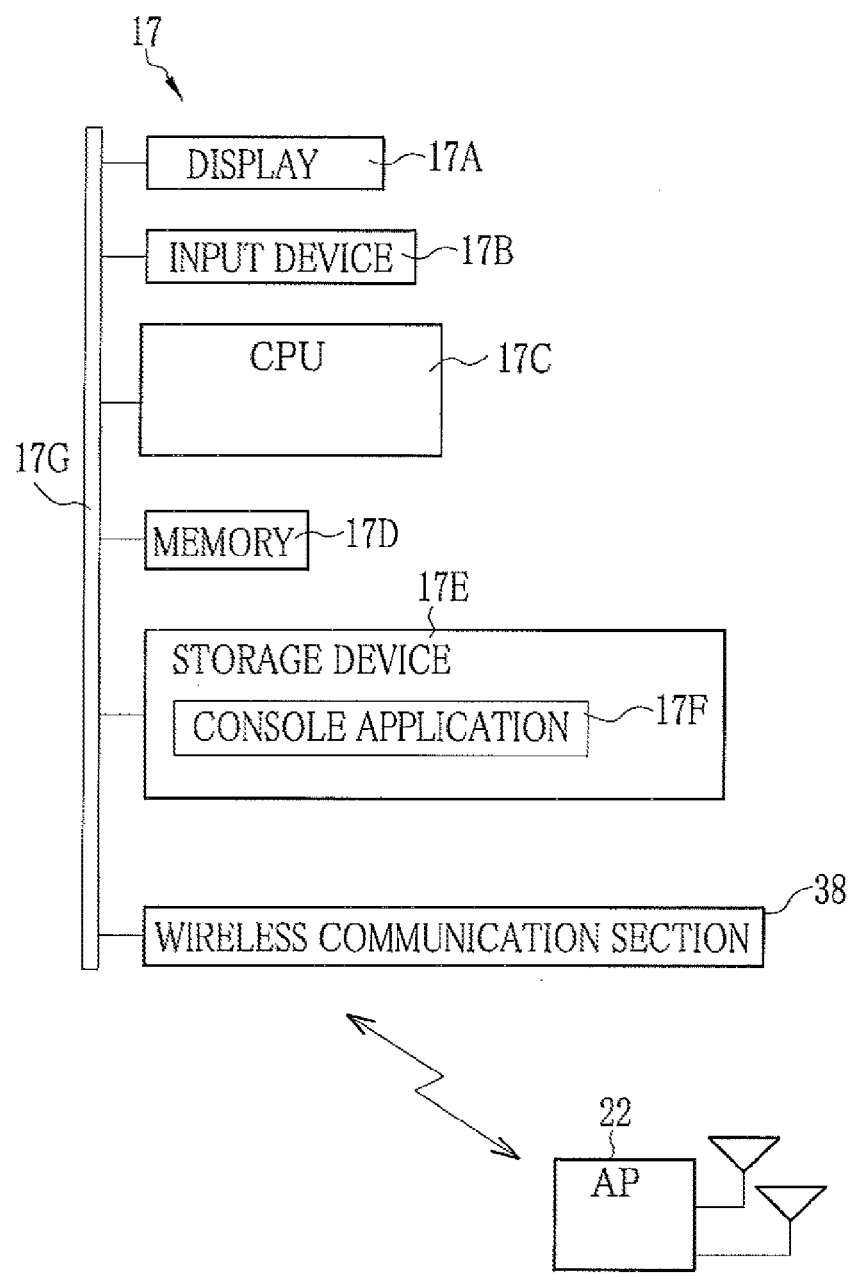
FIG. 5 is a schematic view of a console.

As shown in FIG. 5, the console 17 is composed of a notebook computer, which is a combination of a display 17A and a main body, and programs (e.g. a control program such as an operating system and a console application program (simply referred to as the console application) 17F) installed on the computer. The console application 17F allows the computer to function as the console 17. The console 17 is provided with the display 17A, an input device 17B, a CPU 17C, a memory 17D, a storage device 17E, and the wireless communication section 38, which are connected to each other through a data bus 17G.

The input device 17B is a touch panel, which is a combination of a keyboard, a mouse, and the display 17A. The storage device 17E stores various types of data, and is composed of a hard disk drive, for example. The control program and the console application 17F are stored in the storage device 17E.

The memory 17D is a working memory, which is used by the CPU 17C to execute processing. The CPU 17C loads the control program, which is stored in the storage device 17E, into the memory 17D, and executes the processing in accordance with the program. Thereby the CPU 17C centrally controls each section of the computer. The wireless communication section 38 is a communication interface for wireless connection to the AP 22 and the WAP 36.

Figure 6:
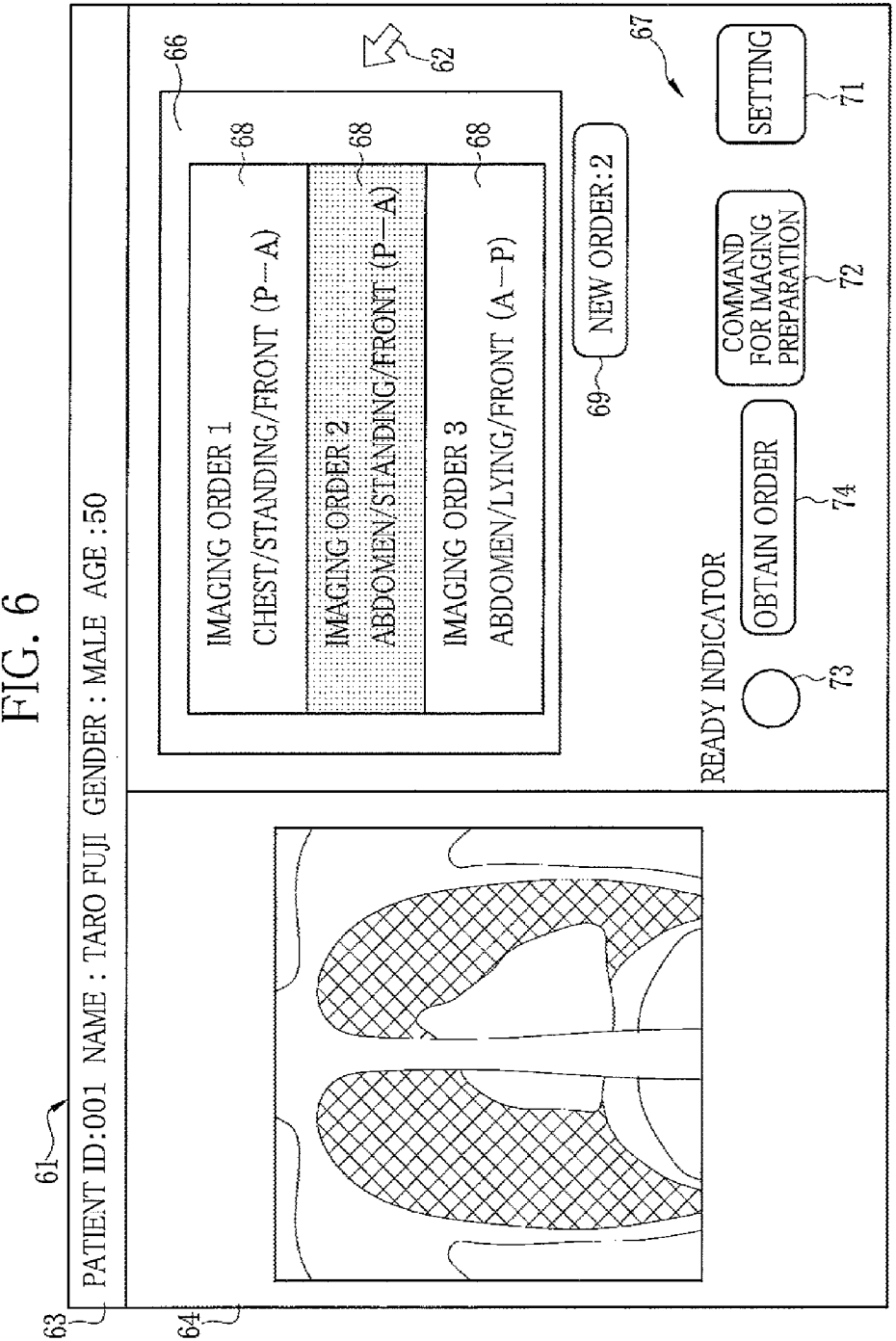
FIG. 6 is an explanatory view of an operation screen of the console.

As shown in FIG. 6, when the console application 17F is started, the display 17A of the console 17 displays an operation screen 61, being a GUI (Graphical User Interface). A pointer 62 for pointing a part of the operation screen 61 is displayed on the operation screen 61. The pointer 62 is operated through an input device such as a mouse or an input pad included in the console 17.

The operation screen 61 is provided with a patient information display area 63, an image display area 64, an order display area 66, and an operation unit display area 67. The order display area 66 displays imaging order(s) 68 received from the RIS server 23. When one of the imaging orders 68 is chosen with the pointer 62, the chosen imaging order 68 is highlighted and displayed distinguishably from the remaining imaging orders 68. The patient information display area 63 displays the patient information (patient name, patient ID, gender, age, and the like) which corresponds to the chosen imaging order 68.

The order display area 66 is provided with a new order indicator 69 that indicates the receipt of new imaging order(s). The "new imaging order" refers to a new or additional imaging order. The new order indicator 69 displays the number of the new imaging orders. The new order indicator 69 allows the operator T to check the presence of the new imaging order(s). The display on the new order indicator 69 disappears upon completion of checking by the operator T, for example, after each of the new imaging orders 68 is chosen with the pointer 62.

The image display area 64 displays an X-ray image which is transmitted from the electronic cassette 16 after the image capture. In FIG. 6, an X-ray image is displayed in the image display area 64 by way of example. Before the image capture, nothing is displayed in the image display area 64. An X-ray image is displayed on the image display area 64 immediately after the image capture, so that the operator T can check the X-ray image to see whether it is appropriately taken. In a case where the imaging order 68 for an already-taken image is chosen from the imaging orders in the order display area 66, the image display area 64 displays an X-ray image which corresponds to the chosen imaging order 68.

The operation unit display area 67 is provided with a setting button 71, an imaging preparation command button 72, a ready indicator 73, and an order obtaining button 74. The setting button 71 is used for making various settings in the electronic cassette 16 or setting the imaging conditions. When the setting button 71 is chosen with the pointer 62, a setting screen is displayed.

The imaging preparation command button 72 is used for transmitting the imaging preparation command to the electronic cassette 16. With the operation of the imaging preparation command button 72, the imaging preparation command is transmitted from the console 17 to the electronic cassette 16. When the control circuit 47 of the electronic cassette 16 receives the imaging preparation command, the control circuit 47 performs a transition process to shift the electronic cassette 16 to the "ready" state. After the completion of the transition process, the control circuit 47 transmits a transition completion signal as a response to the console 17. The ready indicator 73 lights up when the console 17 receives the transition completion signal. The lighted ready indicator 73 indicates that the electronic cassette 16 is in the "ready" state.

The order obtaining button 74 is used for accessing the RIS server 23 to obtain (fetch) the imaging order. When the order obtaining button 74 is operated, a delivery request for the imaging order (hereinafter referred to as the imaging order delivery request) is transmitted to the RIS server 23. The RIS server delivers the new imaging order(s), which has not been obtained.

Figure 7:
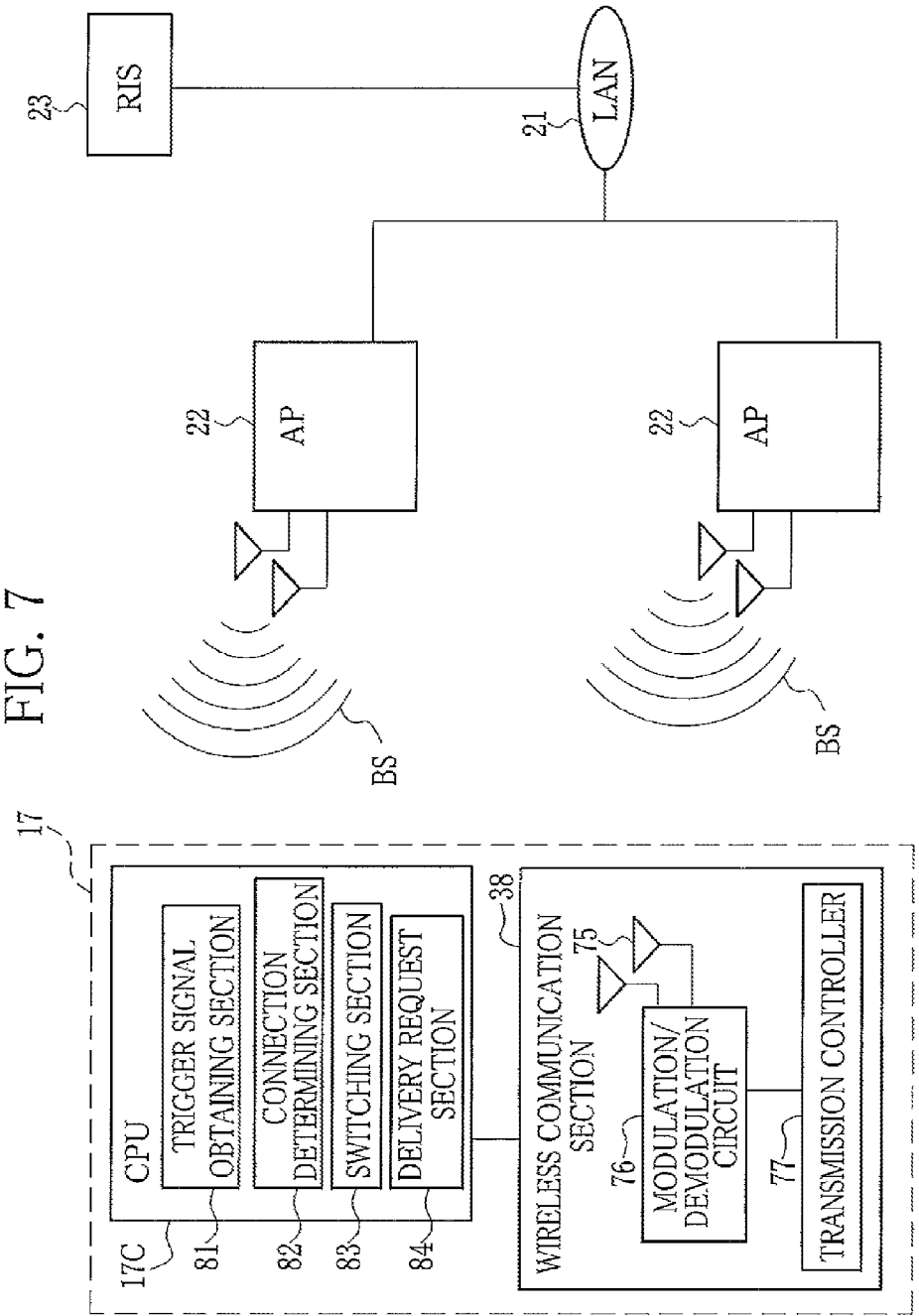
FIG. 7 is an explanatory view of a main part of the console.

As shown in FIG. 7, the wireless communication section 38 of the console 17 is composed of an antenna 75, a modulation/demodulation circuit 76, a transmission controller 77, and the like. The modulation/demodulation circuit 76 performs modulation for impressing the data on a carrier and demodulation for extracting the data from the carrier received by the antenna 75.

The transmission controller 77 performs transmission control compliant with the wireless LAN standard. To be more specific, the transmission controller 77 performs the transmission control in accordance with communications protocol(s) compliant with TCP (Transmission Control Protocol)/IP (Internet Protocol) or IEEE 802.11n. As shown by an OSI (Open Systems Interconnection) reference model, the communications protocols are hierarchical, and the communications protocols at different layers are used in combination. The TCP/IP is communications protocols also used for a cable LAN, and used as upper-layer communications protocols for the wireless LAN standard. The IEEE 802.11n is a communications protocol at a layer level lower than the TCP/IP, and stipulates communication procedure unique to wireless communication. Based on the IEEE 802.11n, radio waves in a frequency band of 2.4 GHz or 5 GHz is used as a wireless communication channel.

Note that the AP 22, the wireless communication section 37 of the electronic cassette 16, the wireless communication section 29 of the source control device 27, and the WAP 36 have substantially the same configuration as the wireless communication section 38, by way of example.

Unlike the cable communication, a communication cable for connection is unnecessary in the wireless communication. Instead, the wireless communication section 38 needs a logical connection to the AP 22. Hereinafter, the connection procedure and communication procedure, which are compliant with the IEEE 802.11n standard and followed by the wireless communication section 38, are described.

Figure 8:
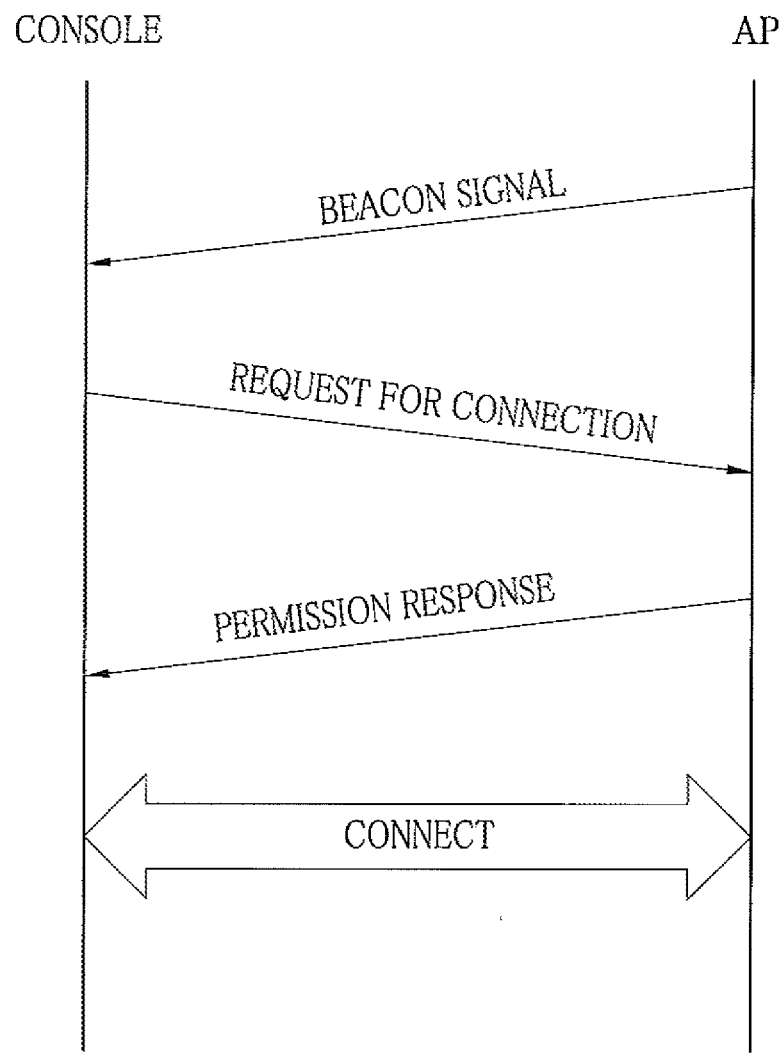
FIG. 8 is a sequence for connecting the console to an AP (access point)

As shown in FIG. 8, in a connection sequence between the wireless communication section 38 of the console 17 and the AP 22, first, the AP 22 transmits radio waves called "beacon signal" (see BS in FIG. 7) at regular time intervals of approximately 100 msec while the AP 22 is on. The beacon signal notifies a wireless terminal such as the console 17, which is located in the environment of the AP 22, of the presence of the AP 22. The wireless communication section 38 of the console 17 constantly monitors the presence or absence of the beacon signal while the console 17 is on, so that the wireless communication section 38 constantly receives the beacon signal when the wireless communication section 38 is within a reception range (coverage) of the beacon signal from the AP 22.

The beacon signal includes a network identifier such as SSID (Service Set Identifier) or ESSID (Extended Service Set Identifier). The network identifier allows the wireless terminal such as the electronic cassette 16 to identify each AP 22 or a network including the APs 22.

The network identifier of each AP 22 in the ward 19 is set to the console 17, so that the console 17 is capable of accessing each AP 22. Upon receiving the beacon signal, the wireless communication section 38 transmits a request (connection request) for connection to the AP 22. The AP 22 performs authentication of the console 17 which transmitted the connection request. For this reason, the console 17 transmits authentication information such as a password, together with the connection request, to the AP 22.

Upon receiving the connection request, the AP 22 matches the received password with the password set in advance, and thereby performs the authentication. In a case where the passwords match, the AP 22 transmits a permission response to the console 17. The permission response includes an IP (Internet Protocol) address assigned to the console 17. When the console 17 receives the permission response, a logical connection link is established, and thus the console 17 is logically connected to the AP 22.

The AP 22 assigns the IP address to the console 17 through the established connection. The console 17 is connected to the LAN 21 through the AP 22, and thereby accesses the RIS server 23 or the image server 24. The high-level communication procedure based on the IP address is performed through steps in accordance with the TCP/IP.

The AP 22 continues transmitting the beacon signal after the connection to the console 17 is established. The console 17 maintains the connection to the AP 22 as long as the console 17 receives the beacon signal from the AP 22. The connection to the AP 22 is terminated when the console 17 is incapable of receiving the beacon signal, for example, when the console 17 is out of the reception range of the beacon signal from the AP 22. The console 17 is reconnected to the AP 22 when or after the console 17 comes within the reception range of the beacon signal and starts receiving the beacon signal again.

The wireless communication section 38 of the console 17 has a roaming function to automatically switch the connection to the AP 22 with high field intensity in a case where the wireless communication section 38 receives the beacon signals from two or more APs 22.

Figure 9:
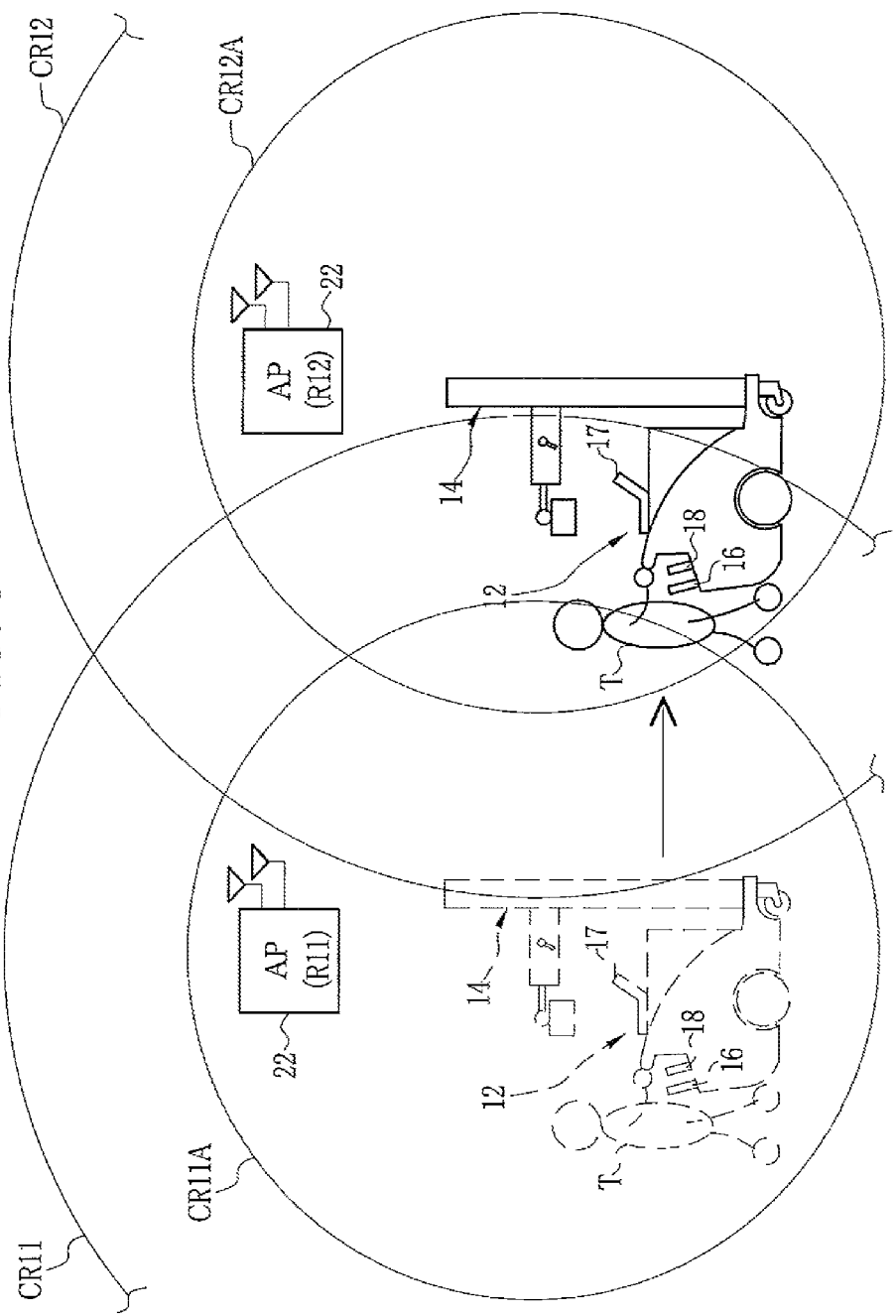
FIG. 9 is an explanatory view of roaming.

For example, as shown in FIG. 9, in a case where the wireless communication section 38 receives the beacon signals from the AP 22 (ID=R11) in the hospital room R11 and the AP 22 (ID=R12) in the hospital room R12, the wireless communication section 38 is connected to the AP 22 with the higher field intensity than the other, based on the field intensity of each of the APs 22. Characters CR11 and CR12 denote communication cells, being the reception ranges, of the radio waves from the APs 22, respectively. In each of the communication cells CR11 and CR12, the radio waves attenuate (decrease) and the field intensity decreases with increasing distance from the corresponding AP 22. To be more specific, in the communication cell CR11, the field intensity is higher in a region CR11A, which is close to the AP 22 (ID=R11), than in a region (outside the CR11A) which is far from the AP 22 (ID=R11). In the communication cell CR12, the field intensity is higher in a region CR12A than in a region outside the CR12A.

First, in the hospital room R11, the console 17 is within the region CR11A in the communication cell CR11 and connected to the AP 22 (ID=R11). The communication cell CR11 partially overlaps the communication cell CR12. In a case where the console 17 together with the mobile radiography unit 14 move from the hospital room R11 to the hospital room R12, the wireless communication section 38 passes through a region at which the region CR11A overlaps a region CR12 to a region at which the communication cell CR11 overlaps a region CR12A. While moving from the hospital room R11 to the hospital room R12, the wireless communication section 38 compares the field intensity of the beacon signal from each AP in the region at which the communication cell CR11 overlaps the communication cell CR12. As the wireless communication section 38 moves, the field intensity of the AP 22 (ID=R12) increases and then becomes higher than the AP 22 (ID=R11) which is currently connected to the wireless communication section 38. Here, in a case where the roaming of the wireless communication section 38 functions normally, the connection is switched to the AP 22 (ID=R12) when the wireless communication section 38 enters the region CR12A.

However, roaming problems of the wireless communication section 38 may occur due to reduction in accuracy of detecting the field intensity and interference of the radio waves from other portable wireless terminals when the console 17 is on the move. The roaming problem of the wireless communication section 38 refers to a malfunction of the roaming of the wireless communication section 38. In the case of the roaming problem, the communication of the wireless communication section 38 becomes unstable, resulting in failure in receiving a new imaging order during the ward round. The console 17 is provided with a mechanism to avoid such roaming problem.

As shown in FIG. 7, when the console application 17F is started, the CPU 17C of the console 17, which works together with the memory 17D and the like, functions as a trigger signal obtaining section 81, a connection determining section 82, a switching section 83, and a delivery requesting section 84.

Figure 10:
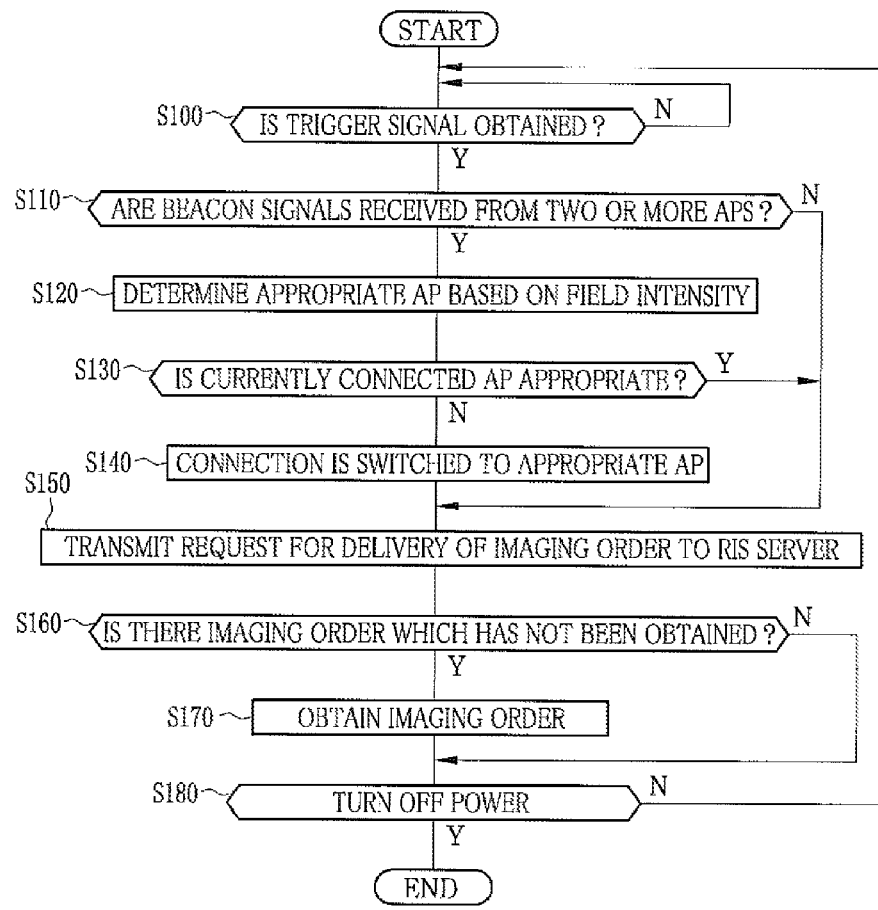
FIG. 10 is a flowchart illustrating procedure of processing of the console.
Figure 11:
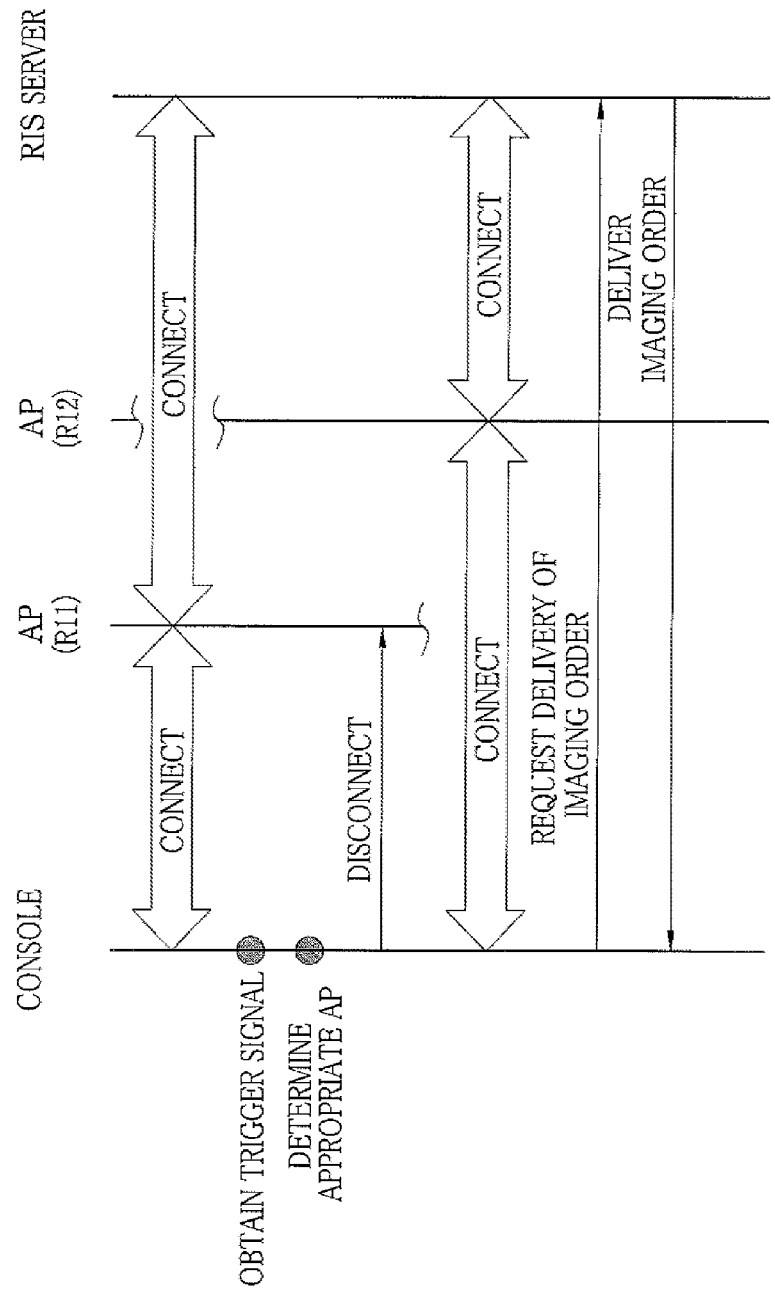
FIG. 11 is a sequence for switching the AP.

As illustrated in a flowchart in FIG. 10 and a timing chart in FIG. 11, the trigger signal obtaining section 81 monitors input of a trigger signal after the console is activated (S100). The trigger signal is transmitted from a trigger signal source in a state where the cart 14a of the mobile radiography unit 14 stands still or stops moving. In this example, the trigger signal obtaining section 81 obtains the trigger signal which is transmitted after the cart 14a stops and before single imaging ends. Here, the single imaging refers to the imaging of a patient performed based on a single imaging order. In this example, the trigger signal refers to an unlocking signal, which is generated when the locking mechanism 33 of the mobile radiography unit 14 is unlocked. The unlocking signal is transmitted from the locking mechanism 33, being the trigger signal source. The locking mechanism 33 is provided in the mobile radiography unit 14 and corresponds to the second transmitting section.

In the work flow of the portable imaging, the locking mechanism 33 is in the locked state while the mobile radiography unit 14 is moved from the cart parking area 15 to the ward 19, as described above. After the mobile radiography unit 14 enters the hospital room and is stopped, the locking mechanism 33 is unlocked to position the X-ray source 26. The unlocking signal is inputted to the trigger signal obtaining section 81 through the wireless communication section 29 of the source control device 27 and the wireless communication section 38 (Y in S100).

When the trigger signal obtaining section 81 obtains the trigger signal, in a case where the wireless communication section 38 receives the beacon signals from the APs 22 (Y in S110), the connection determining section 82 determines one of the APs 22 as the appropriate AP 22 suitable for the connection based on the field intensity (S120). The appropriate AP 22 is suitable in terms of ensuring relatively stable communication quality in connecting to the wireless communication section 38. The connection determining section 82 determines such AP 22 as the appropriate AP 22. To be more specific, the connection determining section 82 obtains field intensities of the beacon signals from the APs 22 through the wireless communication section 38. The connection determining section 82 determines the AP 22 with the highest field intensity, among other APs 22, as the appropriate AP 22. Generally, the higher the field intensity of the beacon signal, the more stable the communication quality of the AP 22 becomes. For this reason, the connection determining section 82 determines the AP 22 with the high field intensity as the appropriate AP 22.

Note that a criterion for determining the appropriate AP 22 may not be a value of the field intensity itself. The criterion may be an evaluation value which corresponds to the field intensity. For example, positional information or distance information of each AP 22 may be estimated from the field intensity, and then the appropriate AP 22 may be determined based on the result of the estimation. Alternatively, test communication may be performed using dummy data. A bit error rate, which indicates the degree of error, or a bit rate, which indicates an amount of communication (rate of communication) per unit time, may be measured. The appropriate AP 22 suitable for the connection may be determined based on the result of the measurement. The bit error rate and the bit rate vary depending on the field intensity. In other words, the bit error rate and the bit rate are evaluation values dependent on the field intensity.

The connection determining section 82 determines the appropriate AP 22 at the timing of obtaining the trigger signal, which is generated in the state where the mobile radiography unit 14 stands still. The wireless communication section 38 of the console 17 measures the field intensity while the mobile radiography unit 14 stands still, so that the measurement is more accurate than that while the mobile radiography unit 14 is on the move. The connection determining section 82 determines the appropriate AP 22 based on the field intensity with high measurement accuracy. Thus, the connection determining section 82 determines the appropriate AP 22 correctly, as compared with the case where the appropriate AP 22 is determined while the mobile radiography unit 14 is on the move.

The switching section 83 determines whether the AP 22 to which the wireless communication section 38 is currently connected is the appropriate AP 22, which is determined by the connection determining section 82 (S130). In a case where the currently connected AP 22 is not the appropriate AP 22 (N in S130), the switching section 83 commands the wireless communication section 38 to switch the connection to the appropriate AP 22 (S140). Upon receiving the command, the wireless communication section 38 disconnects itself from the currently connected AP 22, and connects itself to the appropriate AP 22 through the connection sequence illustrated in FIG. 8. As shown in a timing chart in FIG. 11, the connection is switched from the AP 22 (ID=R11) to the AP (ID=R12), for example. The switching section 83 maintains the connection to the currently connected AP 22 in a case where the currently connected AP 22 is the appropriate AP 22 (Y in S130).

After the connection is switched to the appropriate AP 22, the delivery requesting section 84 transmits the imaging order delivery request (S150). The imaging order delivery request is transmitted through the appropriate AP 22. As illustrated in the timing chart in FIG. 11, the RIS server 23 is constantly connected to every AP 22 through the LAN 21. Upon receiving the imaging order delivery request, the RIS server 23 checks the presence of a new imaging order which has not been obtained by the console 17 (S160). In a case there is a new imaging order (Y in S160), the new imaging order is transmitted through the AP 22 which has transmitted the imaging order delivery request. Since the wireless communication section 38 is connected to the appropriate AP 22, the communication between the console 17 and the RIS server 23 is stable. The console 17 receives the imaging order from the RIS server 23 (S170). The above-described steps are repeated until the console 17 is turned off (S180).

Note that the delivery requesting section 84 transmits the imaging order delivery request every time the trigger signal is obtained, regardless of whether the connection is switched to the AP 22 or not. Since a new imaging order occurs independently of the connection to the appropriate AP 22, increasing the frequency of transmitting the imaging order delivery request allows the console 17 to receive a new imaging order as soon as possible. Furthermore, the delivery requesting section 84 transmits the imaging order delivery request at regular time intervals, regardless of the presence or absence of the trigger signal. In other words, the delivery requesting section 84 transmits the imaging order delivery request at regular time intervals, and in addition, every time the trigger signal is obtained (in this case, regardless of whether the connection is switched). As a result, the frequency of transmitting the imaging order delivery request is increased and thereby failure in receiving the new imaging order is prevented.

Figure 12:
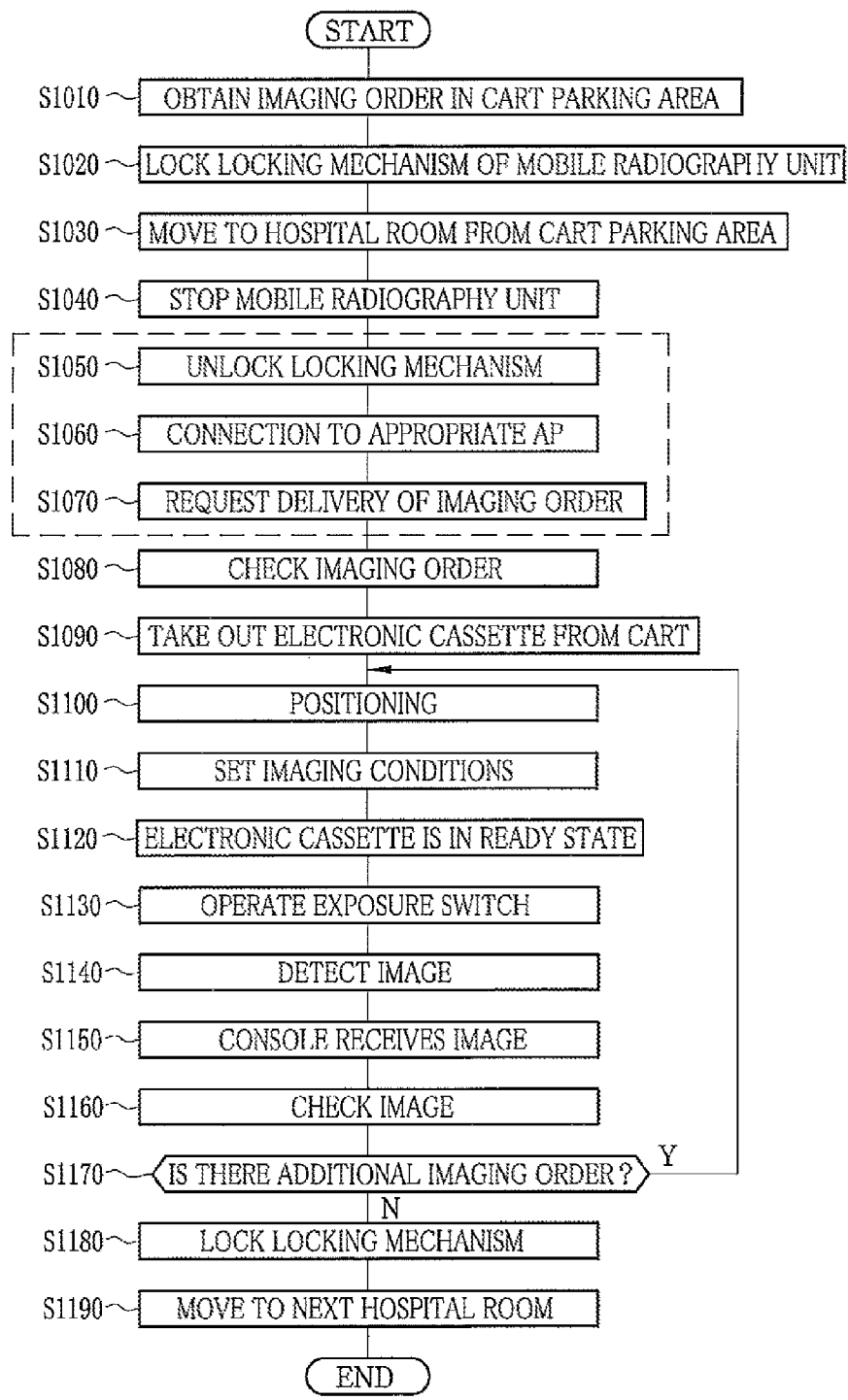
FIG. 12 is a flowchart illustrating an example of a work flow for the portable imaging.

Referring to a flowchart illustrating a work flow of the portable imaging in FIG. 12, an operation of the above configuration is described. To perform the portable imaging, first, the operator T mounts the X-ray imaging apparatus 12, which includes the electronic cassette 16, the console 17, and the functional unit 18, on the mobile radiography unit 14 in the cart parking area 15 (see FIG. 1). Then, the operator T activates the console 17, and connects the console 17 to the LAN outlet 15a through a communication cable.

The order obtaining button 74 on the operation screen 61 (see FIG. 6) of the console 17 is operated. When the order obtaining button 74 is operated, the console 17 transmits the imaging order delivery request to the RIS server 23 through the LAN outlet 15a and the LAN 21. Upon receiving the imaging order delivery request, the RIS server 23 delivers a new imaging order, which has not been obtained by the console 17. Thus the new imaging order for the portable imaging is obtained (S1010). The operator T verifies the imaging order and the hospital room to visit. After being activated, the console 17 starts transmitting the imaging order delivery request at regular time intervals through the wireless communication section 38.

Before moving the mobile radiography unit 14, the operator T checks the position of the lock member 34 to make sure that the locking mechanism 33 is locked so as not to inadvertently displace the X-ray source 26 while the mobile radiography unit 14 is on the move. In a case where the locking mechanism 33 is not locked, the operator T operates the lock member 34 to lock the locking mechanism 33 (S1020). Then, the mobile radiography unit 14 is moved from the cart parking area 15 to the ward 19. When or after the wireless communication section 38 of the console 17 receives the beacon signal from the AP 22 in the ward 19, the wireless communication section 38 establishes the connection to the AP 22 through the connection sequence illustrated in FIG. 8. The mobile radiography unit 14 passes by the AP(s) 22 as the mobile radiography unit 14 moves along. Also, while the mobile radiography unit 14 is on the move, the wireless communication section 38 compares the field intensities of the APs 22 to perform the roaming.

Upon arriving at the hospital room R11 specified by the imaging order, the operator T with the mobile radiography unit 14 enters the hospital room R11 (S1030). The operator T places the mobile radiography unit 14 at a position suitable for imaging the patient P (S1040). Then, preparation for imaging is started. First, the locking mechanism 33 of the mobile radiography unit 14 is unlocked (S1050). When unlocked, the locking mechanism 33 generates the unlocking signal. The unlocking signal is inputted to the source control device 27 in the mobile radiography unit 14. The unlocking signal is transmitted to the console 17 through the wireless communication section 29 of the source control device 27. The trigger signal obtaining section 81 of the console 17 obtains the unlocking signal, which is received by the wireless communication section 38, as the trigger signal.

After the trigger signal obtaining section 81 obtains the trigger signal, the connection determining section 82 determines the appropriate AP 22 suitable for the connection and then the switching section 83 establishes the connection to the appropriate AP 22 (S1060), following the steps illustrated in FIG. 10. In a case where the roaming of the wireless communication section 38 is performed normally during the move of the mobile radiography unit 14, the wireless communication section 38 is supposed to be connecting itself to the AP 22 (ID=R11) in the hospital room R11 upon entering the hospital room R11. This is because the field intensity of the AP 22 (ID=R11) in the hospital room R11 is the highest for the console 17 which is also in the hospital room R11. In this case, the connection determining section 82 determines that the AP 22 (ID=R11), being the currently connected AP 22, is the appropriate AP 22, so that the connection to the AP 22 (ID=R11) is maintained.

In a case where the wireless communication section 38 has a roaming problem, there may be a possibility that the connection to an inappropriate AP 22 is maintained and the connection to the appropriate AP 22 is not established while the mobile radiography unit 14 is moved. In this case, the switching section 83 issues a command for switching the AP 22, to the wireless communication section 38. The wireless communication section 38 switches the connection to the appropriate AP 22 (ID=R11) determined by the connection determining section 82. The connection determining section 82 determines the appropriate AP 22 based on the field intensity which is received by the wireless communication section 38 in the stationary state. Thus, the appropriate AP 22 which ensures the stable communication quality is selected correctly.

The delivery requesting section 84 transmits the imaging order delivery request to the RIS server 23 through the AP 22 (ID=R11) (S1070). In a case where an additional imaging order is present, the additional imaging order is delivered from the RIS server 23. The operator T checks the details of the (already-obtained) imaging order for the patient P in the hospital room R11 and the presence or absence of an additional imaging order through the operation screen 61 on the console 17 (S1080). In a case where there is an additional imaging order, the preparation for imaging is performed in view of the additional imaging order.

The operator T takes out the electronic cassette 16 from the mobile radiography unit 14 and activates the electronic cassette 16 (S1090). Then, the X-ray source 26 and the electronic cassette 16 are positioned as appropriate for a body part which is specified by the imaging order (S1100). For example, in a case where the chest of the patient P is to be imaged, the electronic cassette 16 is placed between the lying patient P and the bed 20 and the position of the electronic cassette 16 is adjusted to correspond to the position of the chest of the patient P. After the positioning of the electronic cassette 16 is completed, the positioning of the X-ray source 26 is performed. Since the locking mechanism 33 is unlocked (see S1020), the operator T moves the arm 32, the column 31, and the X-ray source 26 of the mobile radiography unit 14. Thereby the irradiation position and the irradiation direction of the X-ray source 26 are adjusted to face the electronic cassette 16.

After the completion of the positioning, the imaging conditions are set (S1110). Based on the imaging order, the operator T determines the imaging conditions through the operation screen 61 of the console 17. Upon the operation of the operator T, the determined imaging conditions are transmitted from the console 17 to the electronic cassette 16. Based on the imaging conditions, the electronic cassette 16 sets, for example, processing conditions (a gain of an integration amplifier or the like) of the sensor panel 41.

The operator T operates the operation panel of the X-ray generating apparatus 11 which is incorporated in the mobile radiography unit 14, and thereby sets the irradiation conditions of the X-ray source 26. The irradiation conditions may be set through the wireless communication from the console 17 to the X-ray generating apparatus 11.

After the completion of setting the imaging conditions, when the imaging preparation command button 72 (see FIG. 6) is operated through the operation screen 61 on the console 17, the imaging preparation command is transmitted from the console 17 to the electronic cassette 16. Upon receiving the imaging preparation command, the electronic cassette 16 shifts to the "ready" state (S1120). Thereby the electronic cassette 16 starts the start detecting operation with the use of the detection sensor 56 (see FIG. 4).

The operator T checks the ready indicator 73 on the operation screen 61 to see that the electronic cassette 16 has been shifted to the "ready" state. Then, the operator T operates the exposure switch 28 at proper timing (S1130) after checking that the position of the patient P is appropriate. The X-ray source 26 starts the X-ray irradiation when the exposure switch 28 is operated. When the X-ray irradiation is started, the electronic cassette 16 detects the start of the X-ray irradiation with the use of the detection sensor 56. When the electronic cassette 16 detects the start of the X-ray irradiation, the sensor panel 41 starts the storage operation to detect an image (S1140).

After a lapse of the irradiation time, the X-ray source 26 ends the X-ray irradiation. When the detection sensor 56 detects the end of the X-ray irradiation, the electronic cassette 16 ends the storage operation, and reads out the X-ray image. The X-ray image is transmitted from the wireless communication section 37 to the console 17. The console 17 receives the X-ray image with the use of the wireless communication section 38 (S1150). The operator T verifies the X-ray image received by the console 17 (S1160). Thus, the single imaging is completed.

In a case where there is an additional imaging order for the same patient P (Y in S1170), the above steps are repeated from the step for positioning (S1100), in accordance with the content of the imaging order. In a case there is no additional imaging order, the electronic cassette 16 is mounted on the mobile radiography unit 14, and the locking mechanism 33 of the mobile radiography unit 14 is locked (S1180), and then the mobile radiography unit 14 is headed for the next hospital room (S1190).

As described above, in the work flow of the portable imaging, whether the AP 22 which is connected to the wireless communication section 38 of the console 17 is appropriate is determined in response to the unlocking operation of the locking mechanism 33 after the mobile radiography unit 14 stops in the hospital room in which the portable imaging takes place. The X-ray imaging apparatus 12, which includes the console 17, also stands still when the mobile radiography unit 14 stands still. The connection to the appropriate AP 22 is established based on the trigger signal, which is generated while the X-ray imaging apparatus 12 stands still, so that switching the connection to the appropriate AP 22 is ensured even if there is a roaming problem when the mobile radiography unit 14 is on the move. Consequently, an error in receiving the imaging order due to unstable communication between the RIS server 23 and the console 17 does not occur, and thus failure in receiving a new or additional imaging order is prevented.

Switching the connection to the appropriate AP 22 is performed after the entry to the hospital room and before the end of the single imaging, so that the additional imaging order for the same patient P is handled properly before the operator T and the mobile radiography unit 14 leave the hospital room. There is no need to return to the previous hospital room to perform imaging of the same patient P after the operator T is headed for the next hospital room. Thus, the operator's time and trouble are saved. In this example, the presence or absence of an additional imaging order is checked before the positioning for the first imaging. This allows the operator T to avoid re-positioning, which is a heavy burden for the operator T. Switching the connection to the appropriate AP 22 is performed soon after the entry to the hospital room, so that there is enough time before the positioning. Even if the delivery of the imaging order takes time, the presence or absence of the additional imaging order is checked before the positioning.

In the present invention, the roaming problem is solved by the connection to the appropriate AP based on the trigger signal, which is transmitted in a state where the X-ray imaging apparatus 12 stands still. In other words, the roaming problem is solved by making changes only in the X-ray imaging system 10 that includes the X-ray imaging apparatus 12, for example, by modifying a program of the console 17. There is no need to modify an entire network such as the LAN 21 including the APs 22. Unlike the mobile communication network for mobile phones and the like, the wireless LAN standard does not stipulate the roaming function, which is considered as one of the factors causing the roaming problem in the LAN 21. According to the present invention, the roaming problem in the LAN 21 is avoided by making changes only in the X-ray imaging system 10. The changes are made easily without cost and trouble as compared with the case where the LAN 21 is modified.

As described above, the operator T needs to capture 50 X-ray images or more per day by himself/herself in some instances. Under severe time constraints, re-imaging and re-positioning, due to the failure in receiving a new or additional imaging order, put physical burdens and mental stress on the operator T because the operator T needs to return to the previous hospital room and perform imaging again after obtaining the patient's consent. The positioning or re-positioning of the patient is a heavy burden for both the operator T and the patient who has difficulty in moving his/her body, and requires the operator T's special care. In addition, time constraints increase mental stress on the operator T. According to the present invention, the physical burdens and mental stress on the operator T are reduced.

Second Embodiment

In the above embodiment, the trigger signal is transmitted at the timing of the unlocking operation of the mobile radiography unit 14, by way of example. The timing of transmitting the trigger signal is not limited to the above as long as the trigger signal is transmitted while the X-ray imaging apparatus 12 stands still. It is preferable that the trigger signal is transmitted before the single imaging ends, as in the case of the trigger signal transmitted at the timing of the unlocking operation. Other than that, the trigger signal may be transmitted as described in a second embodiment illustrated in FIG. 13, for example. The second embodiment describes an example in which the trigger signal is generated when the electronic cassette 16 shifts to the "ready" state. Also at this timing, the X-ray imaging apparatus 12 is considered to be still. Also in this case, the trigger signal is transmitted before the single imaging ends.

Figure 13:
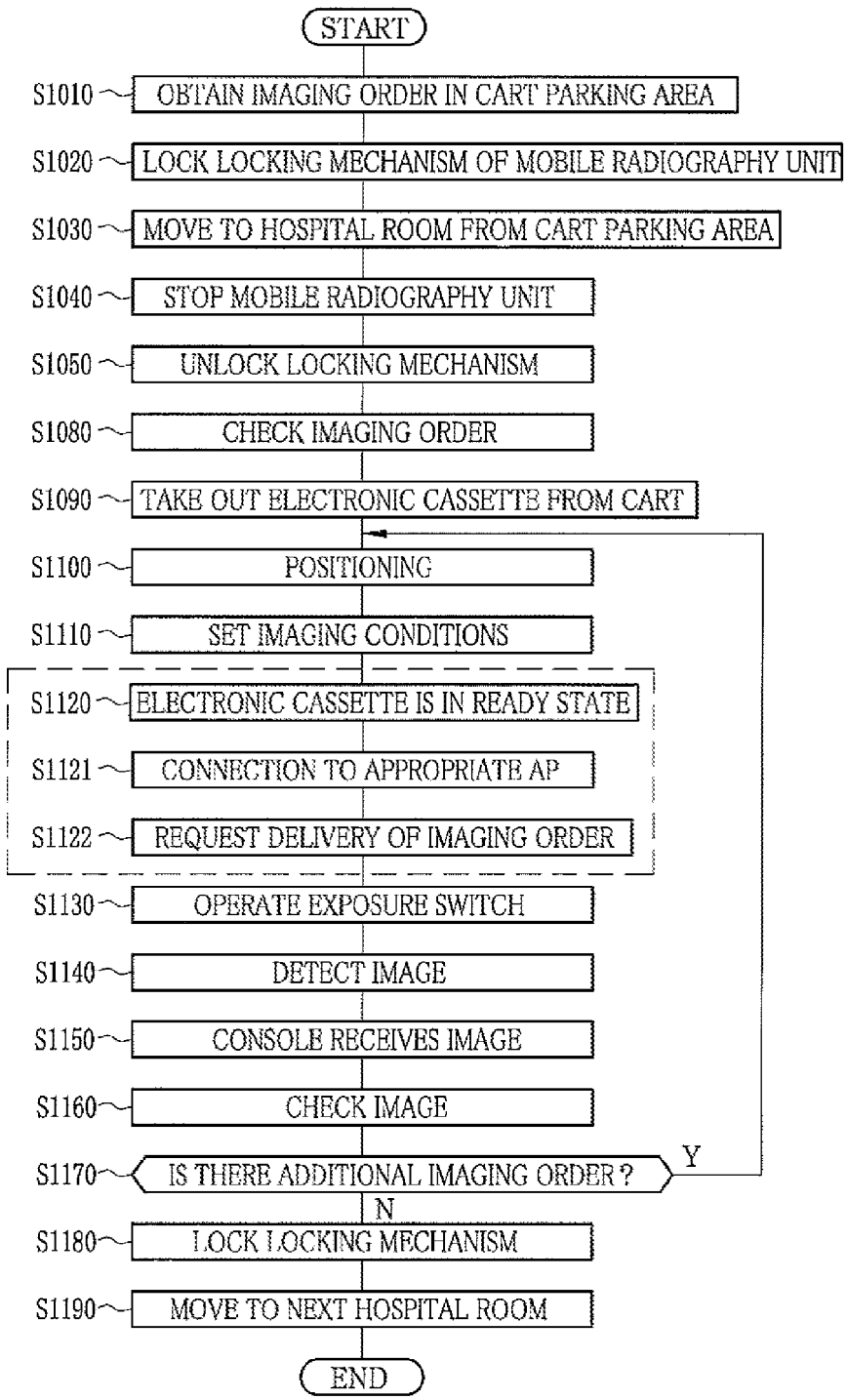
FIG. 13 is a flow chart of a second embodiment.

The steps in a dotted box in FIG. 13 are the only differences between the first and second embodiments. The remaining steps are the same, so that the descriptions thereof are omitted. In this example, the control circuit 47 of the electronic cassette 16 transmits the trigger signal. As described above, upon receiving the imaging preparation command from the console 17, the control circuit 47 allows the sensor panel 41 to shift to the "ready" state (S1120). After the sensor panel 41 is shifted to the "ready" state, the control circuit 47 transmits a shift completion signal to the console 17, notifying that the sensor panel 41 is in the "ready" state. Upon receiving the shift completion signal, the wireless communication section 38 inputs the shift completion signal as the trigger signal to the trigger signal obtaining section 81. Since the control circuit 47 of the electronic cassette 16 constitutes the X-ray imaging apparatus 12, the control circuit 47 corresponds to a first transmitting section that is provided in the X-ray imaging apparatus 12.

After the trigger signal obtaining section 81 obtains the trigger signal, the connection determining section 82 determines the appropriate AP 22 based on the field intensity. In a case where the currently connected AP 22 is not the appropriate AP 22, the switching section 83 commands the wireless communication section 38 to switch the connection to the appropriate AP 22 (S1121). The delivery requesting section 84 transmits the imaging order delivery request to the RIS server 23 (S1122).

In this example, note that the CPU 17C may generate the trigger signal when the imaging preparation command button 72 of the console 17 is operated, and input the trigger signal to trigger signal obtaining section 81. In this case, the CPU 17C corresponds to the first transmitting section.

Third Embodiment

Figure 14:
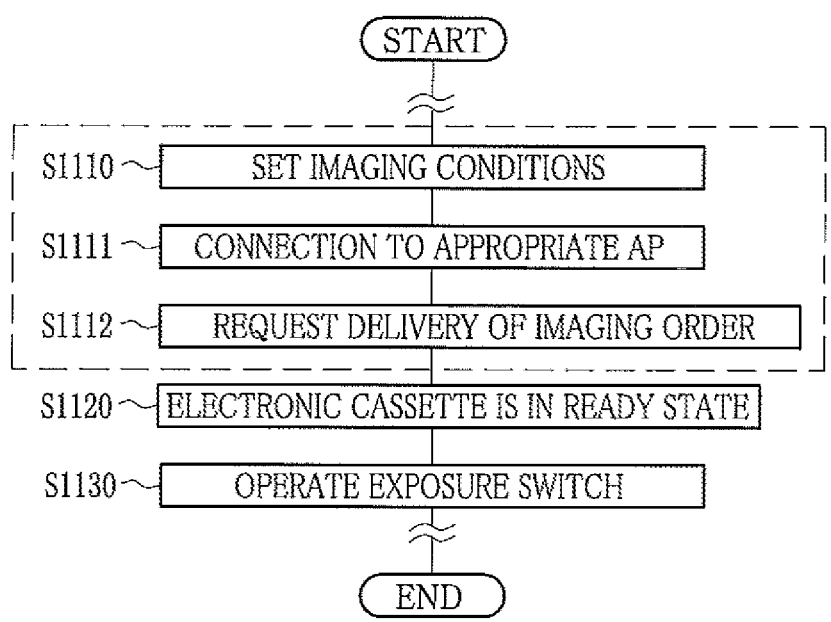
FIG. 14 is a flow chart of a third embodiment.

A third embodiment illustrated in FIG. 14 is an example in which the trigger signal is generated when the console 17 is operated. Also at this timing, the X-ray imaging apparatus 12 is considered to be still. In the third embodiment, for example, the CPU 17C generates the trigger signal when the imaging conditions are set through the operation screen 61 (S1110). Also in this example, the CPU 17C corresponds to the first transmitting section, in a manner similar to the second embodiment. Based on the trigger signal, the appropriate AP 22 is determined and the connection to the appropriate AP 22 is established (S1111) and the imaging order delivery request is transmitted (S1112).

The operation of the console 17 may be, for example, choosing one of imaging orders 68 in the order display area 66, instead of setting the imaging conditions. In a case where the console 17 is a collapsible notebook computer as described in this example, the operation of the console 17 may be opening the notebook computer. The operation of the console 17 may be operating the pointer 62 through a mouse or the like.

Fourth Embodiment

Figure 15:
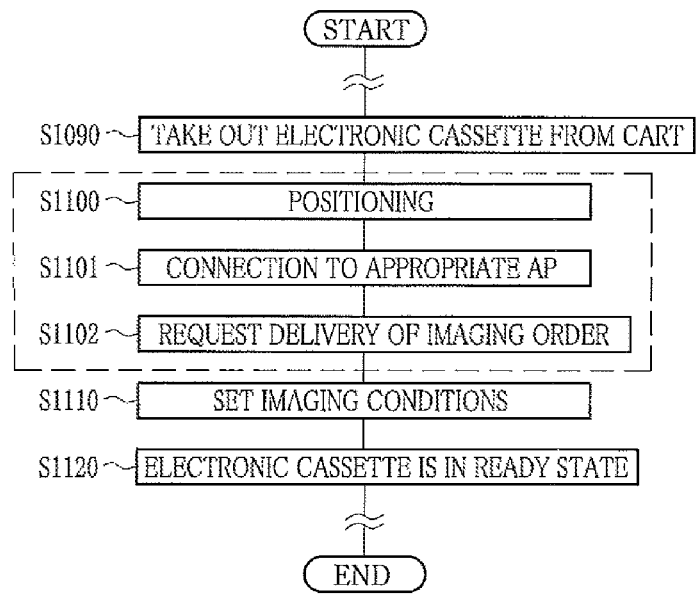
FIG. 15 is a flow chart of a fourth embodiment.

A fourth embodiment illustrated in FIG. 15 is an example in which the trigger signal is generated when the positioning is completed (S1100). After the positioning is completed, the appropriate AP 22 is determined and the connection to the appropriate AP 22 is established (S1101), and then the imaging order delivery request is transmitted (S1102). In this case, for example, a positioning completion button for inputting the completion of the positioning is provided on the operation screen 61 of the console 17. Upon the operation of the positioning completion button, the CPU 17C inputs the trigger signal to the trigger signal obtaining section 81. Also in this case, the CPU 17C corresponds to the first transmitting section, in a manner similar to the third embodiment.

Note that the positioning completion button may be provided on the electronic cassette 16 or the mobile radiography unit 14. In this case, notification of completion of positioning is transmitted to the console 17. The trigger signal obtaining section 81 obtains the notification of completion of positioning as the trigger signal. In a case where the notification of completion of positioning is transmitted from the electronic cassette 16, the electronic cassette 16 corresponds to the first transmitting section. In a case where the notification of completion of positioning is transmitted from the mobile radiography unit 14, the mobile radiography unit 14 corresponds to the second transmitting section.

Figure 16:
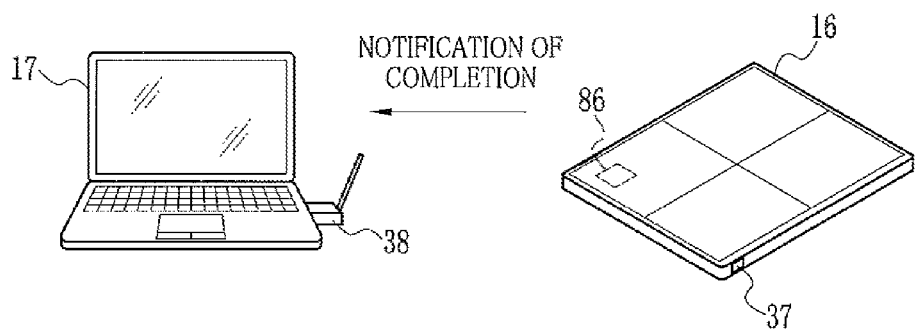
FIG. 16 is an explanatory view of the fourth embodiment.

As shown in FIG. 16, a completion detection sensor 86 for detecting the completion of the positioning may be provided instead of the positioning completion button. For example, the electronic cassette 16 may have an acceleration sensor as the completion detection sensor 86. The position of the electronic cassette 16 is changed during the positioning but the electronic cassette 16 stands still after the positioning is completed. The acceleration sensor detects that the electronic cassette 16 stands still, and determines that the positioning is completed after the electronic cassette 16 remains standing still for a predetermined period of time. Then, the notification of completion of positioning is transmitted from the electronic cassette 16.

A device for transmitting/receiving ultrasound signals may be provided as the completion detection sensor to each of the electronic cassette 16 and the X-ray source 26. The device for transmitting/receiving the ultrasound signals detects that the electronic cassette 16 is placed to face the X-ray source 26, and determines that the positioning is completed.

Fifth Embodiment

Figure 17:
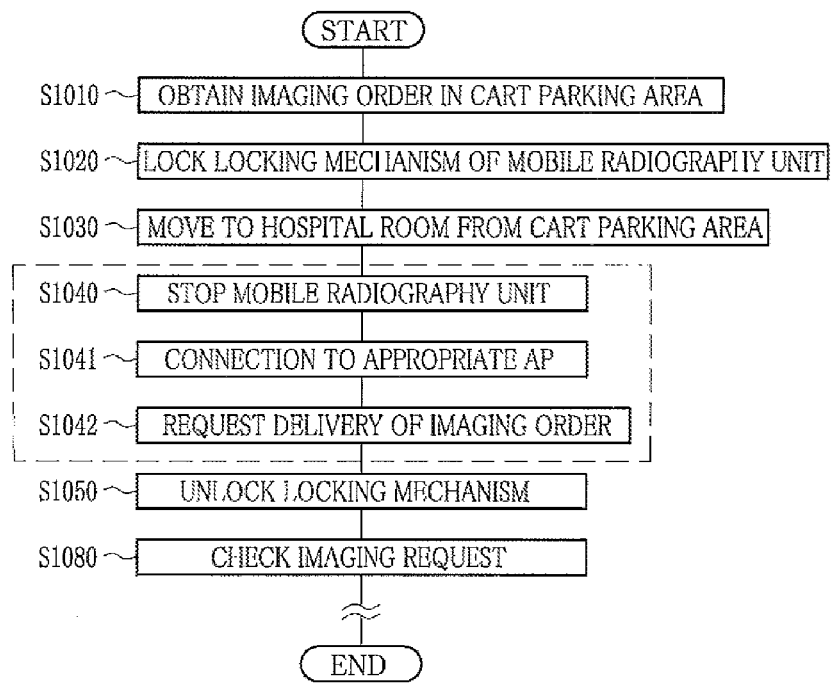
FIG. 17 is a flow chart of a fifth embodiment.
Figure 18:
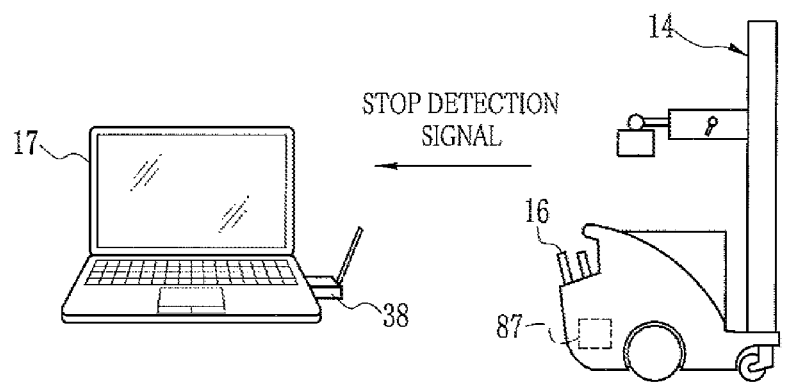
FIG. 18 is an explanatory view of the fifth embodiment.

A fifth embodiment shown in FIGS. 17 and 18 is an example in which a trigger signal is generated when the mobile radiography unit 14 stops (S1040). In this case, as shown in FIG. 18, the mobile radiography unit 14 is provided with a stop sensor 87. The stop sensor 87 detects the state of rotation of the wheels of the mobile radiography unit 14. For example, the stop sensor 87 is a photo sensor. The stop sensor 87 transmits a stop detection signal to the console 17 in a case where the rotation of the wheels is stopped. The trigger signal obtaining section 81 obtains the stop detection signal as the trigger signal. After the trigger signal is obtained, the appropriate AP is determined and the connection to the appropriate AP is established (S1041), and then the imaging order delivery request is transmitted (S1042). In this example, the stop sensor 87 corresponds to the second transmitting section.

Note that a sensor for detecting application of a foot brake may be used as the stop sensor 87 in a case where the mobile radiography unit 14 has a foot brake.

Sixth Embodiment

Figure 19:
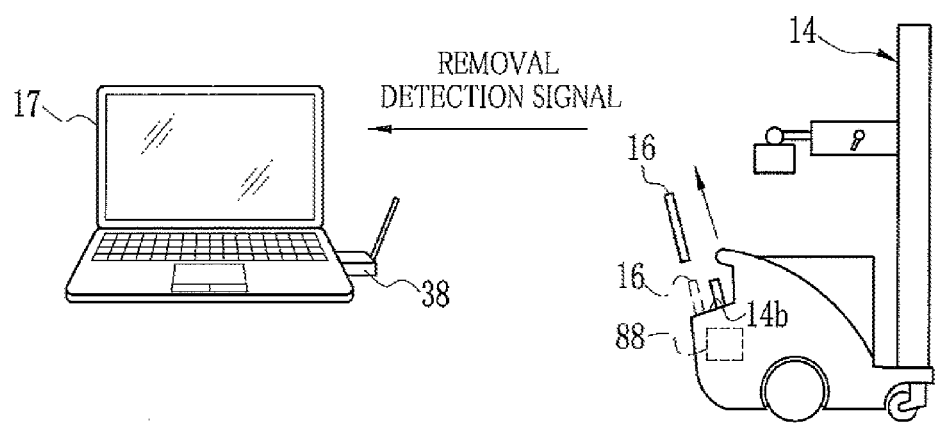
FIG. 19 is an explanatory view of a sixth embodiment.

A sixth embodiment shown in FIG. 19 is an example in which a trigger signal is generated when the electronic cassette 16 is taken out of the mobile radiography unit 14. The mobile radiography unit 14 is provided with an accommodation section 14b for accommodating the electronic cassette 16. The accommodation section 14b is provided with a removal detection sensor 88 that detects removal of the electronic cassette 16 from the accommodation section 14b. The removal detection sensor 88 is, for example, a photo sensor or a detection switch for detecting motion of a movable part. The removal detection sensor 88 transmits a removal detection signal when the electronic cassette 16 is taken out of the accommodation section 14b. The removal detection signal is transmitted to the console 17. The console 17 inputs the removal detection signal as a trigger signal to the trigger signal obtaining section 81. In this example, the removal detection sensor 88 corresponds to the second transmitting section.

Timing for generating the trigger signal may differ from those in the above embodiments. For example, the trigger signal may be generated when the console 17 receives the radiation image from the electronic cassette 16 (S1150) or when the exposure switch 28 is operated (S1130), as shown in the work flow for the portable imaging in FIG. 12. In a case where the electronic cassette 16 has the function to detect the start and the end of the X-ray irradiation, the trigger signal may be generated at the timing of detecting the start or the end of the X-ray irradiation.

In the work flow for the portable imaging shown in FIG. 12, the trigger signal is generated in a state where the mobile radiography unit stands still, after the mobile radiography unit enters the hospital room. The trigger signal may be generated in any of the steps before the single X-ray imaging ends. As described above, the first embodiment describes an example in which the trigger signal is generated in response to the step (S1050) for unlocking the locking mechanism 33, of the steps included in the work flow for the portable imaging illustrated in FIG. 12. The second embodiment describes an example in which the trigger signal is generated in response to the step (S1120). In the step (S1120), the electronic cassette 16 shifts to the "ready" (ready for imaging) state. The trigger signal may be generated in response to any of the steps illustrated in FIG. 12. However, in consideration of occurrence of re-positioning, it is preferable to check an additional imaging order before the positioning. Hence, it is preferable to generate the trigger signal in response to the step performed after the entry to the hospital room and before the positioning.

In the combination of the above embodiments, the trigger signals may be generated in response to two or more steps. The determination of the AP 22, the switching of the AP 22, and requesting the delivery of the imaging order may be performed based on the respective trigger signals. Effectiveness of preventing failure in receiving the imaging order increases as the transmission frequency of the imaging order delivery requests increases. The trigger signal may be transmitted from the first transmitting section of the X-ray imaging apparatus 12 or the second transmitting section of the mobile radiography unit 14. Both the first and second transmitting sections may be provided. Trigger signals transmitted at different timing from different transmitting sections may be selectively used. A combination of the trigger signals of different types may be selectably used.

In each of the above embodiments, the wireless LAN standard (IEEE 802.11n) is described by way of example. Another wireless LAN standard, for example, IEEE 802.11a, IEEE 802.11b, or the next-generation of IEEE 802.11ac may be used. As described above, unlike the mobile communication network of the mobile phones or the like, some of the wireless LAN standards do not stipulate roaming functions. For this reason, the need for the present invention is increasing.

The X-ray imaging apparatus 12 is composed of the electronic cassette 16, the console 17, and the functional unit 18, by way of example. The functional unit 18 may be incorporated in the electronic cassette 16 or the console 17. The function of the console 17 may be incorporated in the mobile radiography unit 14. The mobile radiography unit 14 which is communicable with the X-ray imaging apparatus 12 is described as an example of the mobile X-ray generating apparatus. The mobile X-ray generating apparatus may not be communicable with the X-ray imaging apparatus. For example, the X-ray imaging system of the present invention may be a combination of an X-ray imaging apparatus and a conventional mobile X-ray generating apparatus (mobile X-ray generating apparatus for X-ray films and IP cassettes) without communication function. As described in the above embodiments, it is easy to use an X-ray imaging apparatus in combination with the conventional mobile X-ray generating apparatus in a case where the electronic cassette has the function to detect the start of the X-ray irradiation. In a case where the first transmitting section, which is incorporated in the X-ray imaging apparatus 12, is used for transmitting the trigger signal, the present invention is applicable even if the communication with the X-ray generating apparatus is not feasible.

Seventh Embodiment

Figure 20:
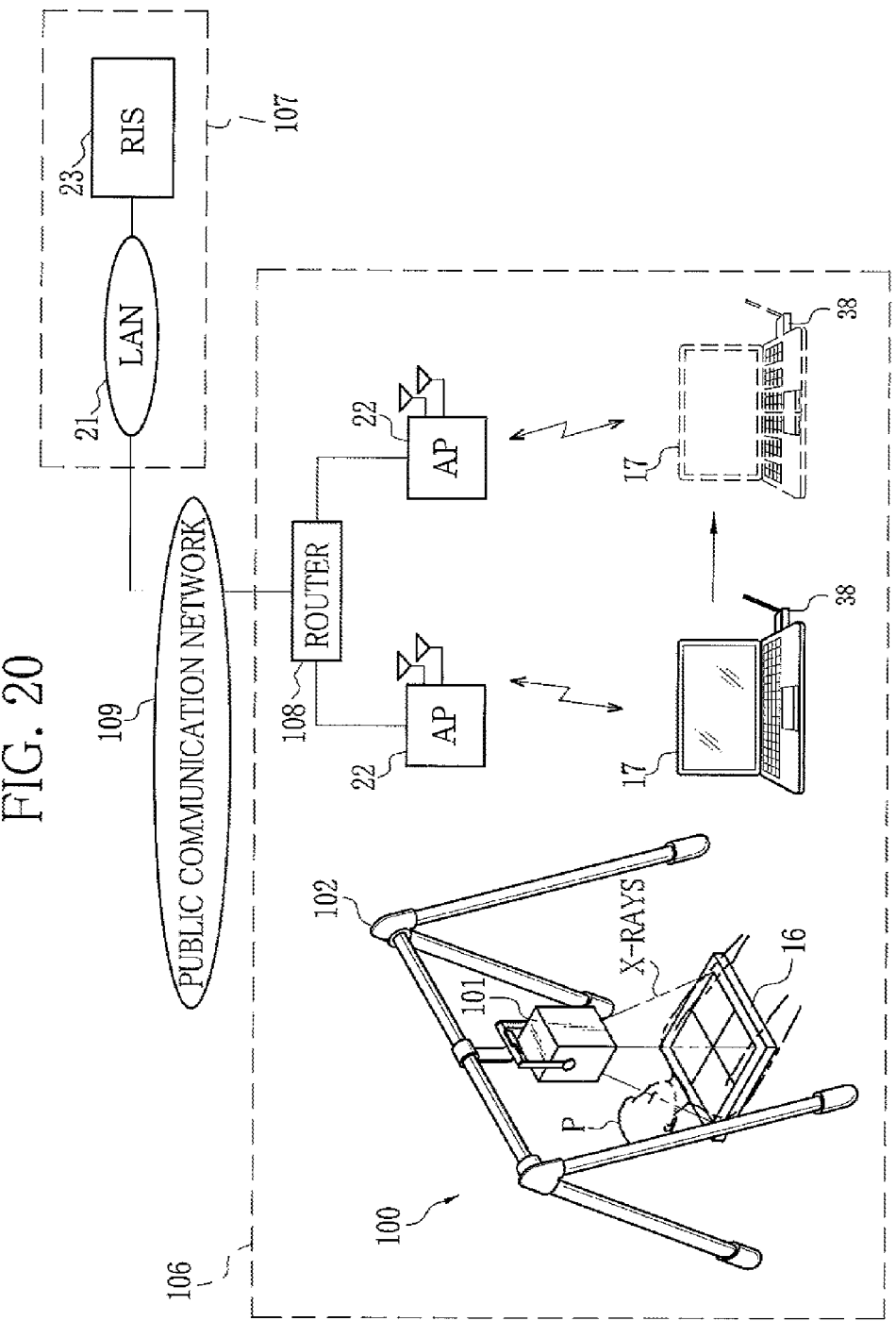
FIG. 20 is an explanatory view of a seventh embodiment.

In the above embodiments, the portable X-ray imaging system, being the combination of the movable X-ray generating apparatus and the X-ray imaging apparatus 12, is described. The movable X-ray generating apparatus (the mobile radiography unit 14) having a movable cart is used as the portable X-ray generating apparatus by way of example. As shown by an X-ray imaging system 100 in a seventh embodiment in FIG. 20, the present invention is also applicable to a portable X-ray imaging system which is a combination of a mobile X-ray generating apparatus 101 without the cart and the X-ray imaging apparatus 12.

In the mobile X-ray generating apparatus 101, an X-ray source and a source control device are accommodated in a portable housing. A support 102 supports the mobile X-ray generating apparatus 101. The mobile X-ray generating apparatus 101 is hung on the support 102 to face the patient P in a lying position. The mobile X-ray generating apparatus 101 is attached to the support 102 in a detachable manner.

The X-ray imaging system 100 is used for visiting care at a care center 106 or a temporary medical office at a site of a disaster, for example. In the care center 106, the LAN 21 is composed of the APs 22 and a router 108, for example. The roaming problem may occur while the X-ray imaging system 100 is moved from room to room of the patients, to perform the portable imaging.

The console 17 of the X-ray imaging apparatus 12 accesses the RIS server 23 of a hospital 107 through the AP 22 which is provided in the care center 106, and thereby receives an imaging order. The AP 22 is connected to the RIS server 23 through the router 108 and a public communication network 109. The public communication network 109 is composed of a public telephone network, WAN (Wide Area Network), Internet, or the like.

The console 17 obtains a trigger signal from a trigger signal source when the console 17 is operated (see FIG. 14), or when the positioning of the electronic cassette 16 is completed (see FIG. 15), or when the electronic cassette 16 is shifted to the "ready" state (see FIG. 13), for example. After the console 17 obtains the trigger signal, the console 17 determines or selects the appropriate AP 22 suitable for the connection, and connects itself to the appropriate AP 22 through the wireless communication section 38. After being connected to the appropriate AP 22, the console 17 accesses the RIS server 23 and receives the imaging order. As described in the above embodiments, the trigger signal is generated only when the X-ray imaging apparatus 12, including the console 17, stands still. Thereby, the console 17 is connected to the appropriate AP 22 without the roaming problem e.g. the roaming problem occurring while the console 17 is on the move.

Note that at least one of the console 17, the electronic cassette 16, and the mobile X-ray generating apparatus 101 may be provided with a stop sensor for detecting that the console 17, the electronic cassette 16, and/or the mobile X-ray generating apparatus 101 stands still. The signal from the stop sensor may be used as the trigger signal. For example, an acceleration sensor is used as the stop sensor.

The present invention is not limited to the above embodiments and may take various forms as long as it is within the scope of the present invention. For example, the above-described embodiments may be combined with each other or with various modified examples. The present invention is not limited to the case where X-rays are used. The present invention is applicable to the case where another type of radiation, for example gamma rays, is used.

What is claimed is:
1. A portable radiation imaging apparatus used in combination with a portable radiation generating apparatus, the portable radiation imaging apparatus capable of accessing an imaging order managing device through an access point, being a wireless relay station, and obtaining an imaging order, the imaging order being information of a request for radiation imaging, the imaging order managing device managing the imaging order, the portable radiation imaging apparatus comprising:
- a wireless communication section for receiving radio waves from the access point and establishing connection to the access point;
- a trigger signal obtaining section for obtaining a trigger signal at least one time from a trigger signal source for transmitting the trigger signal, in a state where the portable radiation imaging apparatus stands still;
- a connection determining section for obtaining the trigger signal and then determining one of the access points as an appropriate access point based on field intensity in a case where the wireless communication section receives the radio waves from the access points;
- a switching section for commanding the wireless communication section to switch the connection to the appropriate access point in a case where the wireless communication section is not connected to the appropriate access point, and allowing the wireless communication section to maintain the connection in a case where the wireless connection section is connected to the appropriate access point; and
- a delivery requesting section for transmitting a delivery request for the imaging order to the imaging order managing device through the wireless communication section in a state where the wireless communication section is connected to the appropriate access point.

2. The portable radiation imaging apparatus according to claim 1, wherein the trigger signal source is at least one of a first transmitting section provided in the portable radiation imaging apparatus and a second transmitting section provided to the portable radiation generating apparatus.

3. The portable radiation imaging apparatus according to claim 2, further comprising:
- an electronic cassette for detecting a radiation image; and
- a console having a function to display the imaging order and the radiation image.

4. The portable radiation imaging apparatus according to claim 3, wherein the console has the wireless communication section, the trigger signal obtaining section, the connection determining section, the switching section, the delivery requesting section, and a function to receive the imaging order.

5. The portable radiation imaging apparatus according to claim 3, wherein the first transmitting section transmits the trigger signal when the electronic cassette is ready for imaging.

6. The portable radiation imaging apparatus according to claim 3, wherein the first transmitting section transmits the trigger signal when the console is operated.

7. The portable radiation imaging apparatus according to claim 3, wherein the trigger signal obtaining section obtains the trigger signal, which is transmitted from the second transmitting section, through communication with the portable radiation generating apparatus.

8. The portable radiation imaging apparatus according to claim 7, wherein the portable radiation generating apparatus is a movable radiation generating apparatus comprising a radiation source for applying radiation and a cart on which the radiation source is mounted.

9. The portable radiation imaging apparatus according to claim 8, wherein the movable radiation generating apparatus has a locking mechanism for limiting displacement of the radiation source while the cart is moved, and the second transmitting section transmits the trigger signal when the locking mechanism is unlocked.

10. The portable radiation imaging apparatus according to claim 8, wherein the movable radiation generating apparatus has a stop sensor for detecting that the cart is stopped, and the second transmitting section transmits the trigger signal when the stop sensor detects that the cart is stopped.

11. The portable radiation imaging apparatus according to claim 8, wherein the movable radiation generating apparatus has an accommodation section for accommodating the electronic cassette and a removal detection sensor for detecting that the electronic cassette is taken out of the accommodation section, and the second transmitting section transmits the trigger signal when the removal detection sensor detects that the electronic cassette is taken out.

12. The portable radiation imaging apparatus according to claim 3, wherein the first transmitting section or the second transmitting section transmits the trigger signal when positioning of the electronic cassette relative to a subject is completed.

13. The portable radiation imaging apparatus according to claim 2, wherein the first transmitting section or the second transmitting section transmits the trigger signal at least one time after the portable radiation imaging apparatus stops moving and before single imaging ends.

14. The portable radiation imaging apparatus according to claim 2, wherein the first transmitting section or the second transmitting section transmits the trigger signal in response to at least one of steps, before an end of single imaging, included in a work flow of portable imaging.

15. The portable radiation imaging apparatus according to claim 14, wherein the steps are those performed before positioning of the electronic cassette.

16. The portable radiation imaging apparatus according to claim 1, wherein the delivery requesting section transmits the delivery request at regular time intervals regardless of presence or absence of the trigger signal.

17. A portable radiation imaging system comprising a portable radiation generating apparatus and a portable radiation imaging apparatus used in combination with the portable radiation generating apparatus, the portable radiation imaging apparatus capable of accessing an imaging order managing device through an access point, being a wireless relay station, and obtaining an imaging order, the imaging order being information of a request for radiation imaging, the imaging order managing device managing the imaging order, the portable radiation imaging system comprising:
- a wireless communication section for receiving radio waves from the access point and establishing connection to the access point;
- a trigger signal obtaining section for obtaining a trigger signal at least one time from a trigger signal source for transmitting the trigger signal, in a state where the portable radiation imaging apparatus stands still;
- a connection determining section for obtaining the trigger signal and then determining one of the access points as an appropriate access point based on field intensity in a case where the wireless communication section receives the radio waves from the access points;
- a switching section for commanding the wireless communication section to switch the connection to the appropriate access point in a case where the wireless communication section is not connected to the appropriate access point, and allowing the wireless communication section to maintain the connection in a case where the wireless connection section is connected to the appropriate access point; and a delivery requesting section for transmitting a delivery request for the imaging order to the imaging order managing device through the wireless communication section in a state where the wireless communication section is connected to the appropriate access point.

* * * * *